United States Patent
Kim et al.

(10) Patent No.: US 10,373,706 B2
(45) Date of Patent: Aug. 6, 2019

(54) VARIETY IDENTIFICATION-ENCODING SYSTEM AND ENCODING METHOD USING THE SAME

(71) Applicant: REPUBLIC OF KOREA (MNGMNT: RURAL DEVEL. ADMIN.), Gyeonggi-do (KR)

(72) Inventors: Yul Ho Kim, Gyeonggi-do (KR); Hyang Mi Park, Gyeonggi-do (KR); Tae Young Hwang, Gyeonggi-do (KR); Sun Lim Kim, Seoul (KR); Seong Bum Baek, Gyeonggi-do (KR); Young Up Kwon, Gyeonggi-do (KR); Wook Hwan Kim, Gyeonggi-do (KR); Sang Jong Lim, Seoul (KR)

(73) Assignee: REPUBLIC OF KOREA (MANAGEMENT: RURAL DEVELOPMENT ADMINISTRATION), Gyeonggi-Do (KR)

(*) Notice: Subject to any disclaimer, the term of this patent is extended or adjusted under 35 U.S.C. 154(b) by 165 days.

(21) Appl. No.: 14/901,922

(22) PCT Filed: Oct. 30, 2013

(86) PCT No.: PCT/KR2013/009731
§ 371 (c)(1),
(2) Date: Dec. 29, 2015

(87) PCT Pub. No.: WO2015/046661
PCT Pub. Date: Apr. 2, 2015

(65) Prior Publication Data
US 2016/0196382 A1  Jul. 7, 2016

(30) Foreign Application Priority Data
Sep. 26, 2013  (KR) .......................... 10-2013-0114326

(51) Int. Cl.
| | | |
|---|---|---|
| G01N 33/48 | (2006.01) | |
| G01N 33/50 | (2006.01) | |
| G16B 30/00 | (2019.01) | |
| C12Q 1/6895 | (2018.01) | |

(52) U.S. Cl.
CPC .......... *G16B 30/00* (2019.02); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2002/0142345 A1* 10/2002 Nelsen .................... C40B 30/04
435/7.1

FOREIGN PATENT DOCUMENTS

| KR | 10-2002-0095793 | 12/2002 |
|---|---|---|
| KR | 10-0426467 | 4/2004 |
| KR | 10-2013-0010172 | 1/2013 |
| KR | 10-2013-0091434 | 8/2013 |
| WO | 2013/023220 | 2/2013 |

OTHER PUBLICATIONS

Craig et al. Ordering of cosmid clones covering the Herpes simplex virus type I (HSV-I) genomes: a test case for fingerprinting by hybridisation. Nucleitc Acids Research, vol. 18, pp. 2653-2660. (Year: 1990).*

Liu, B. et al. "Development of InDel markers for *Brassica rapa* based on whole-genome re-sequencing", Theor Appl Genet, 126:231-239 (2013).

Shen, Y-J. et al."Development of Genome-Wide DNA Polymorphism Database for Map-Based Cloning of Rice Genes", Plant Physiology, 135:1198-1205 (2004).

International Search Report dated Jun. 24, 2014 in corresponding International Application No. PCT/KR2013/009731.

Lestari, Puji et al., "Single Nucleotide Polymorphisms and Haplotype Diversity in Rice Sucrose Synthase 3", *Journal of Heredity*, 2011, vol. 102, No. 6, pp. 735-746.

Zhang, Wei et al., "Species-Specific Identification from Incomplete Sampling: Applying DNA Barcodes to Monitoring Invasive Solanum Plants", *PLoS One*, 2013, vol. 8, Issue 2, Article e55927, pp. 1-7.

* cited by examiner

*Primary Examiner* — Russell S Negin
(74) *Attorney, Agent, or Firm* — Wenderoth, Lind & Ponack, L.L.P.

(57) ABSTRACT

Provided is a variety identification-encoding system, including: a chromosome-decoding module decoding a chromosome of a reference genome variety and a chromosome of a target variety; a variation region-detecting module detecting a variation region in the decoded chromosome through single nucleotide variation dense region analysis; an amplification result-acquiring module setting an indel marker in the detected variation region and amplifying the indel marker by a polymerase chain reaction (PCR) to acquire an amplification result; and an encoding module encoding the amplification result.

8 Claims, 22 Drawing Sheets

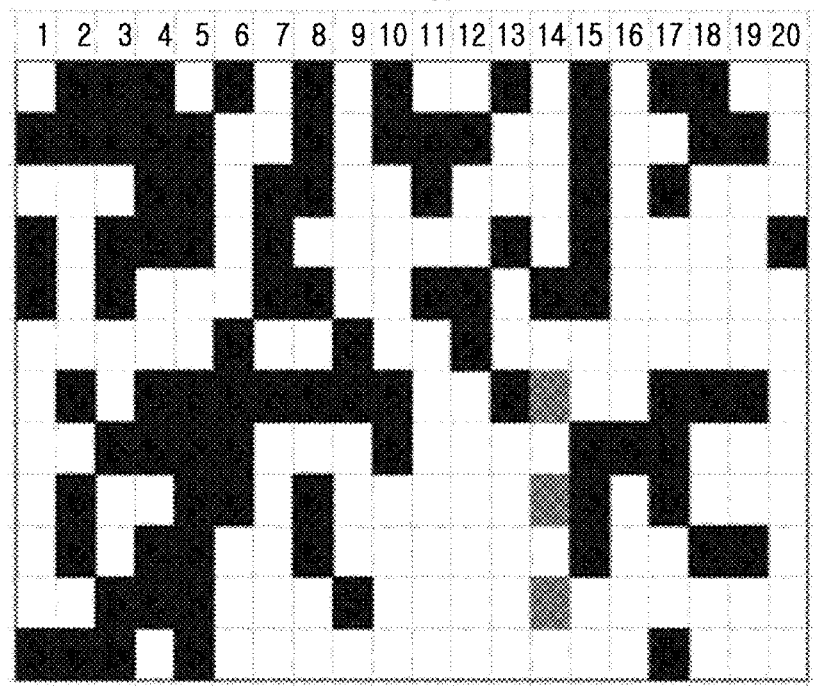
(Cheongja)
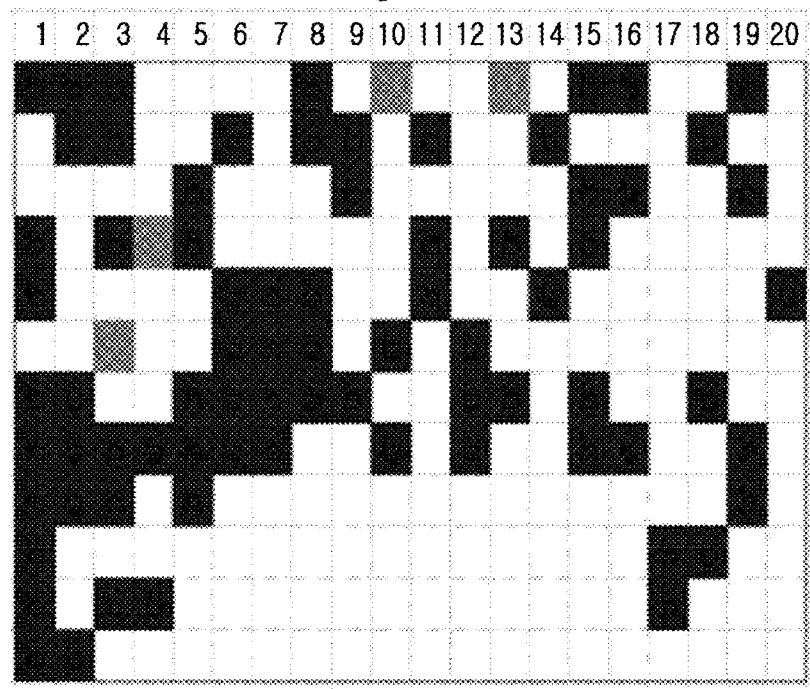
(Pungwon)
FIG. 11A

VARIETY IDENTIFICATION-ENCODING SYSTEM AND ENCODING METHOD USING THE SAME

TECHNICAL FIELD

The present invention relates to a variety identification-encoding system and an encoding method using the same, and, more particularly, to a variety identification-encoding system in which a specific indel marker in a variation region of a genome of a variety is selected, and the amplification result thereof is encoded to indentify the variety, and an encoding method using the same.

BACKGROUND ART

Recently, with the advance of information and communication industries, research and development of biometrics for identifying a target person have been actively conducted. Biometrics includes methods of using physical characteristics, such as iris, finger print, and DNA, and methods of behavioral characteristics, such as signature, voice, and gait. Meanwhile, even in the case of crops, procedures for securing the rights of developed varieties have become important through the strengthening of intellectual property rights or the like, and thus there has been a desperate need for variety identification technologies, such as personal identification cards.

For the identification of crop varieties, methods of classifying varieties using the morphological characteristics of plants, such as grass type, leaf shape, and grain size, based on the expertise and experience of breeders have been generally used. However, since the morphological characteristics thereof are greatly influenced by environmental changes, such as climate changes, recently, variety identification technologies using DNA markers having no influence on environment, such as simple sequence repeats (SSR) and sequence tagged sites (STS), have been developed. However, these variety identification technologies are problematic in that it is difficult to classify the recurrent parent varieties having high genetic similarity, like qualities bred by backcross, and in that these technologies have limitations in the usage of quality identification technologies because a small number of markers are used.

In order to overcome such problems, recently, technologies for identifying a variety at a genetic level using next-generation sequencing (NGS) have been developed. However, these technologies using NGS are disadvantageous in that high cost and much time are required. Therefore, it is extremely necessary that a variety identification system that can be performed at a general laboratory level be developed.

In the related art, Korean Patent Registration No. 10-0426467 discloses an encoding method for identifying the variety of crops. However, in this method, only two-digit numerical codes for identifying rice varieties are given, and a system for selecting an indel marker for variety identification and encoding the amplification result thereof is not disclosed. Therefore, it is still difficult to classify varieties having high genetic similarity, such as backcrossed varieties.

Further, Korean Unexamined Patent Publication No. 10-2013-0010172 discloses a method of identifying lettuce varieties using a microsatellite primer set. However, in this method, a system for selecting an indel marker for variety identification and encoding the indel marker to express the result thereof in a two-dimensional manner. Therefore, it is still difficult to identify the lettuce varieties at a glance.

DISCLOSURE

Technical Problem

Accordingly, the present inventors intend to develop a variety identification system which can identify varieties bred by backcross and can be performed at a general laboratory level by performing research on a molecular marker that can be efficiently used for variety identification and an encoding system thereof.

Therefore, an object of the present invention is to provide a variety identification-encoding system.

Specifically, the encoding system is intended to select a specific indel marker in a variation region of a genome of a variety and encode the amplification result thereof to indentify the variety.

Further, the encoding system is intended to output the encoded result by a one-dimensional expression or a two-dimensional expression.

Further, the encoding system is intended to be applied to a variety breeding lineage tree.

Further, the encoding system is intended to identify varieties having very high genetic similarity by applying this encoding system to varieties bred by backcross.

Moreover, the encoding system is intended to investigate the degree of variety immobilization.

Meanwhile, another object of the present invention is to provide an encoding method for variety identification using the system.

Technical Solution

In order to accomplish the above objects, an aspect of the present invention provides a variety identification-encoding method, including the steps of: (a) decoding a chromosome of a reference genome variety and a chromosome of a target variety using a chromosome-decoding module; (b) detecting a variation region in the decoded chromosome through single nucleotide variation dense region analysis using a variation region-detecting module; (c) setting an indel marker in the detected variation region and amplifying the indel marker by a polymerase chain reaction (PCR) to acquire an amplification result, using an amplification result-acquiring module; and (d) encoding the amplification result using an encoding module.

Preferably, in the step (c), the amplification result may be represented by "a" when the band size of an amplification result of the reference genome variety is the same as the band size of an amplification result of the target variety, and may be represented by "b" when the band size of the amplification result of the reference genome variety is different from the band size of the amplification result of the target variety.

Preferably, the step (d) may include the step of: (d1) converting the amplification result "a" into a digital signal "0" to be marked with white, and converting the amplification result "b" into a digital signal "1" to be marked with black.

Preferably, the method may further include the step of: (e) outputting the encoded result by a one-dimensional expression or a two-dimensional expression using the output module after the step (d1).

Preferably, the step (e) may include the step of: outputting the phenotype of the target variety together with the encoded result.

Preferably, two or more target varieties may be used, and the step (e) may be a step of outputting two or more encoded results of the two or more target varieties.

Preferably, the two or more encoded results may be represented by a two-dimensional expression, and information about a female or male variety thereof may be outputted as a lineage tree.

Preferably, the step (e) may include the steps of: outputting the two or more encoded results by a two-dimensional expression and detecting regions having the differences between the two or more two-dimensional expressions; and marking the detected regions with colors other than white and black to distinguish backcrossed varieties and recurrent parent varieties and output these varieties.

Preferably, the step (e) may include the steps of: outputting the two or more encoded results by a two-dimensional expression and detecting hetero regions; and marking the hetero regions with colors other than white and black to distinguish a degree of immobilization of varieties and output these varieties.

Another aspect of the present invention provides a variety identification-encoding system, including: a chromosome-decoding module decoding a chromosome of a reference genome variety and a chromosome of a target variety; a variation region-detecting module detecting a variation region in the decoded chromosome through single nucleotide variation dense region analysis; an amplification result-acquiring module setting an indel marker in the detected variation region and amplifying the indel marker by a polymerase chain reaction (PCR) to acquire an amplification result; and an encoding module encoding the amplification result.

Preferably, the amplification result-acquiring module may acquire the amplification result as "a" when the band size of an amplification result of the reference genome variety is the same as the band size of an amplification result of the target variety, and may acquire the amplification result as "b" when the band size of the amplification result of the reference genome variety is different from the band size of the amplification result of the target variety.

Preferably, the encoding module may convert the amplification result "a" into a digital signal "0" to be marked with white, and may convert the amplification result "b" into a digital signal "1" to be marked with black.

Preferably, the system according to the present invention may further include: an output module outputting the result encoded by the encoding module a by one-dimensional expression or a two-dimensional expression.

Preferably, the system may further include: a phenotype input module receiving a phenotype of the target bean variety and transmitting the phenotype thereof to the output module.

Preferably, the output module may output two or more encoded results of the two or more target varieties.

Preferably, the output module may output the two or more encoded results by a two-dimensional expression, and may output information about a female or male variety thereof as a lineage tree.

Preferably, the output module may output the two or more encoded results by a two-dimensional expression, and may detect regions having the differences between the two or more two-dimensional expressions to mark the detected regions with colors other than white and black.

Preferably, the output module may output the two or more encoded results by a two-dimensional expression, and may detect hetero regions to mark the hetero regions with colors other than white and black.

Advantageous Effects

According to the variety identification-encoding system of the present invention, the identification of varieties can be easily performed even at a general laboratory level, and the competitiveness of the domestic agricultural industry can be improved by protecting domestic varieties and breeders and promoting the branding of varieties.

Further, according to the present invention, varieties can be quickly and objectively identified by converting gene information into digital signals.

Further, according to the present invention, the gene information for variety identification can be expressed in a two-dimensional manner as well as in a one-dimensional manner, and thus DMB-specific patterns for each chromosome can be understood at a glance.

Further, according to the present invention, since the information about female or male varieties to be identified can be outputted as a lineage tree, the degree of recombination of varieties can be easily recognized, and thus varieties can be more effectively identified.

Further, according to the present invention, since backcrossed varieties and recurrent parent varieties can be classified, the conventional limitation in variety identification using a molecular marker can be overcome, and thus the two kinds of varieties having very high genetic similarity can also be identified.

Further, according to the present invention, since the degree of immobilization of varieties can be recognized due to further expression of a hetero region, the rapid immobilization of separating and breeding lines becomes possible, and thus the present invention can contribute to the uniformity and stability of varieties.

Furthermore, according to the present invention, the analyses of similarity between varieties, population structures, and the like can be effectively performed because a bin map can be created at a chromosome level, and the change of a variation region (DMB) at a chromosome level can be quickly detected because the investigation of recombination patterns of newly-breeding varieties becomes possible.

DESCRIPTION OF DRAWINGS

Figure 5A:
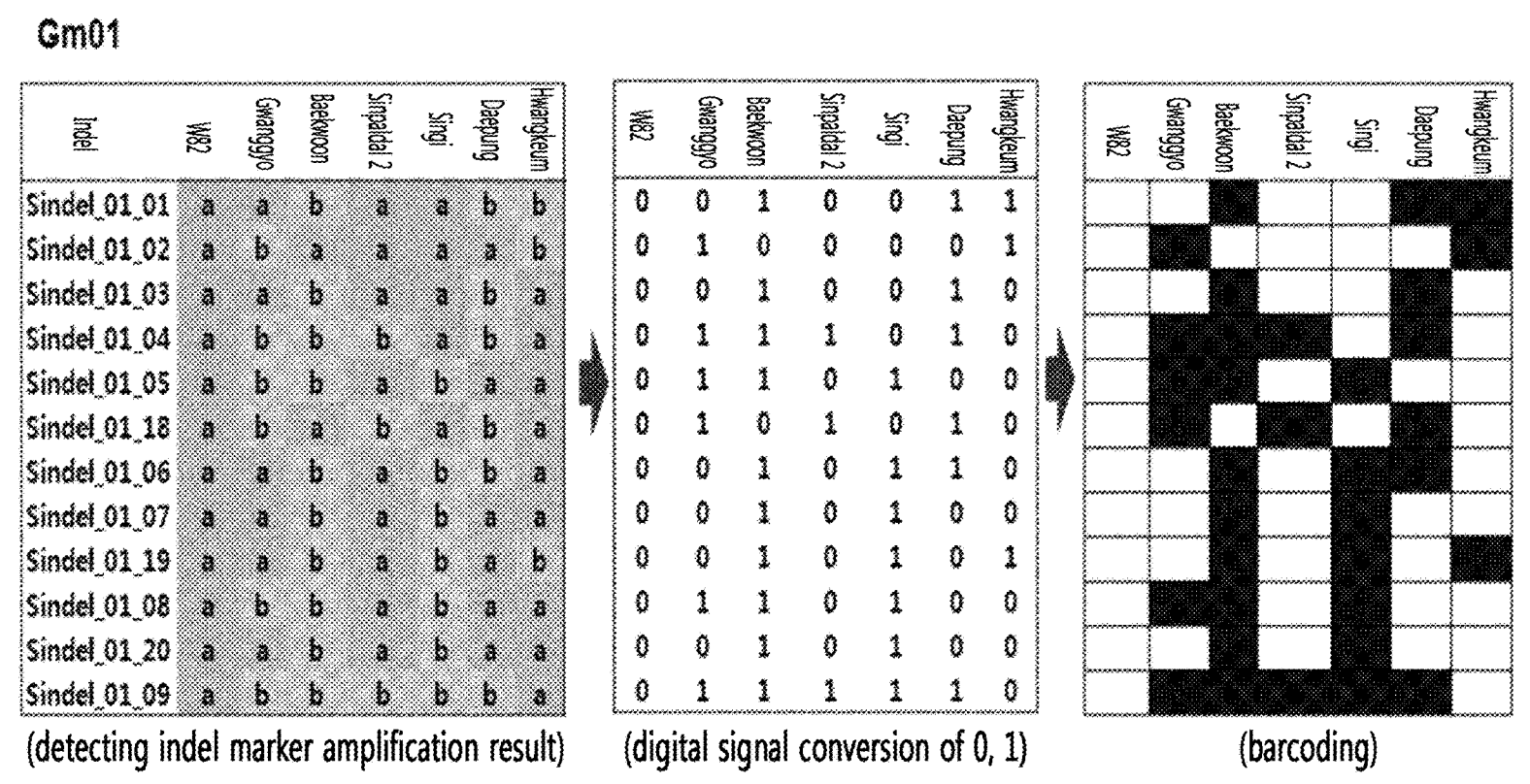
Figure 5B:
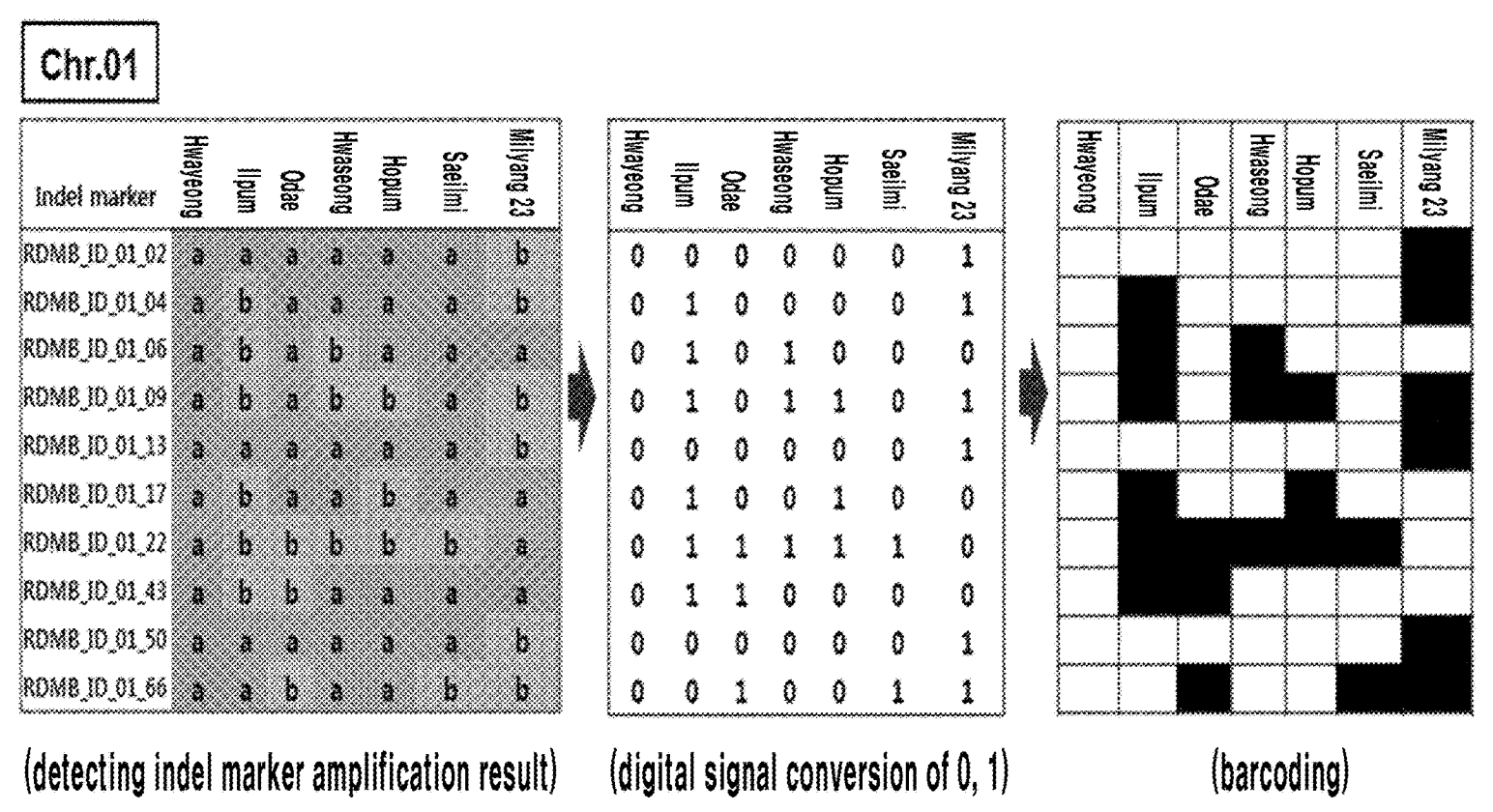

FIG. 5A is a view showing a process of encoding the amplification results of indel markers in chromosome 1 of seven kinds of bean varieties.

FIG. 5B is a view showing a process of encoding the amplification results of indel markers in chromosome 1 of seven kinds of rice varieties.

Figure 10A:
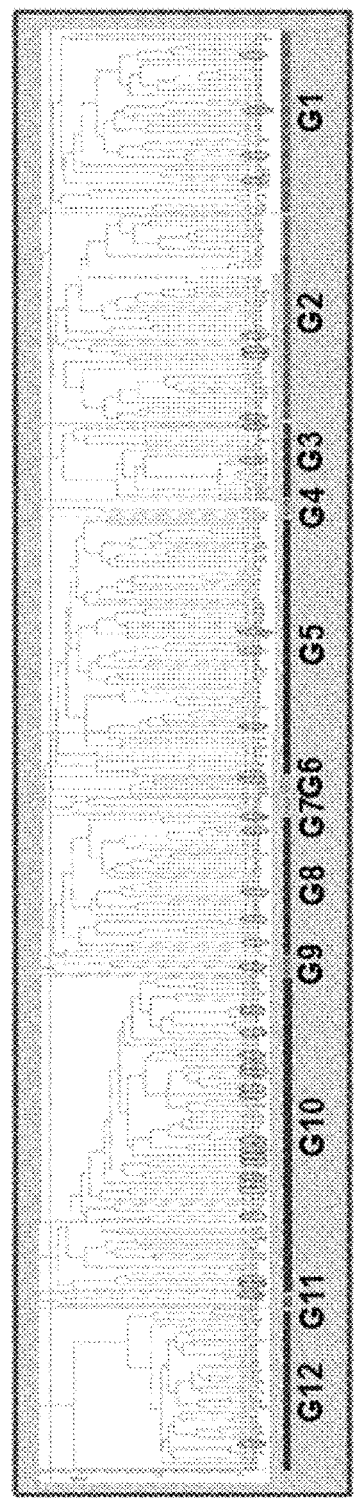
FIG. 10A is a view showing a case where genetic similarity between genetic rice varieties can be determined using the variety identification-encoding system of the present invention. Here, genetic rice varieties are classified into twelve groups at a genetic similarity of 0.68.
Figure 10B:
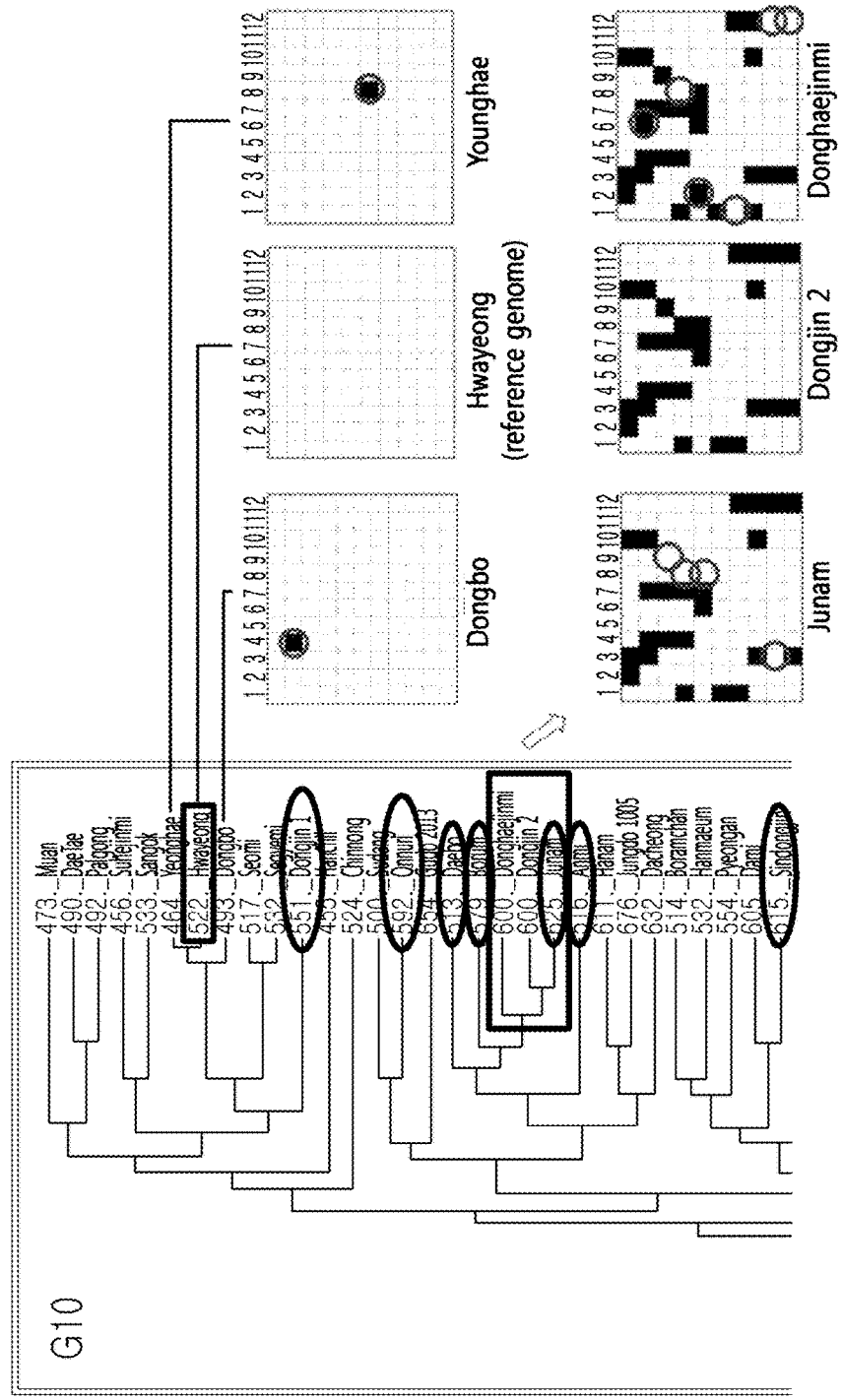
Figure 10C:
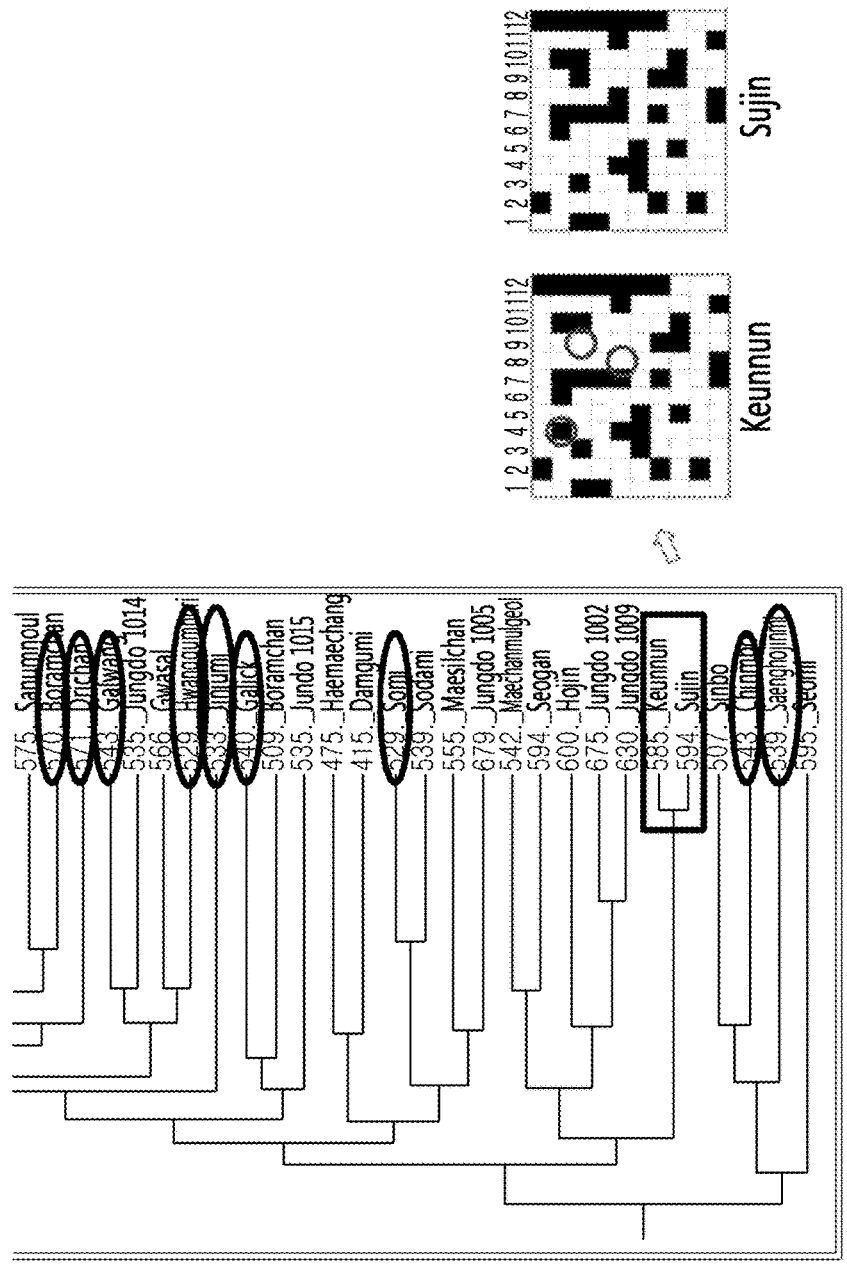

Each of FIGS. 10B and 10C is a view showing an example in which the variety identification-encoding system of the present invention is applied to Group 10 (G10: rice) having high genetic similarity. Here, regions the same as Hwayeongbyeo are marked with white, and regions different from Hwayeongbyeo are marked with black.

FIG. 11A is a view showing an example in which the degree of immobilization of bean varieties is determined using the variety identification-encoding system of the present invention. Here, regions the same as Williams 82 are marked with white, regions different from Williams 82 are marked with black, and hetero regions are marked with colors other than white and black.

Figure 11B:
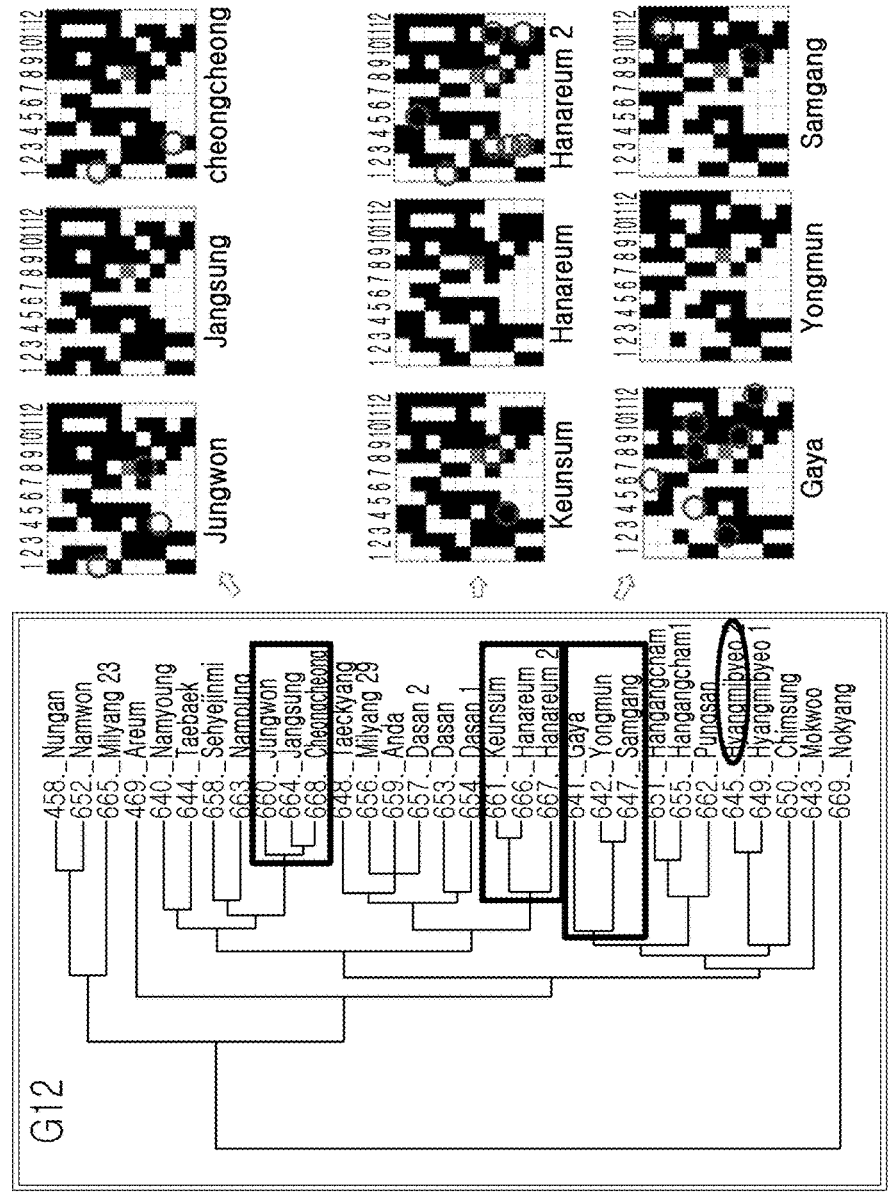

FIG. 11B is a view showing an example in which the variety identification-encoding system of the present invention is applied to Group 12 (G10: rice) having high genetic similarity. Here, regions the same as Hwayeongbyeo are marked with white, regions different from Hwayeongbyeo are marked with black, and hetero regions are marked with colors other than white and black.

Figure 12A:
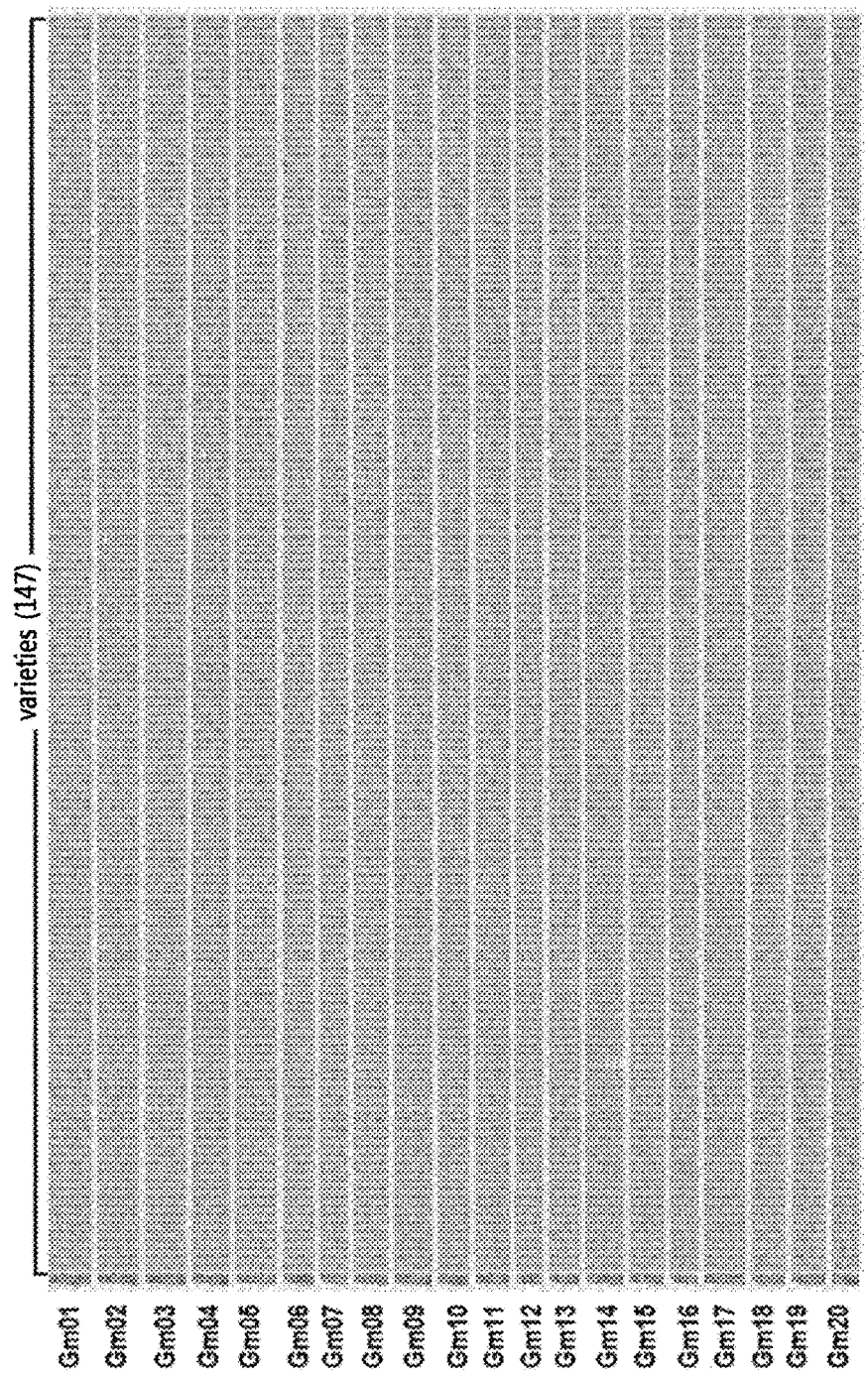

FIG. 12A is a view showing a bin map created at a chromosome level based on the identification data about 147 bean varieties constructed using the variety identification-encoding system of the present invention. Here, PCR results the same as Williams 82 and PCR results different from Williams 82 are marked with different colors, respectively.

Figure 12B:
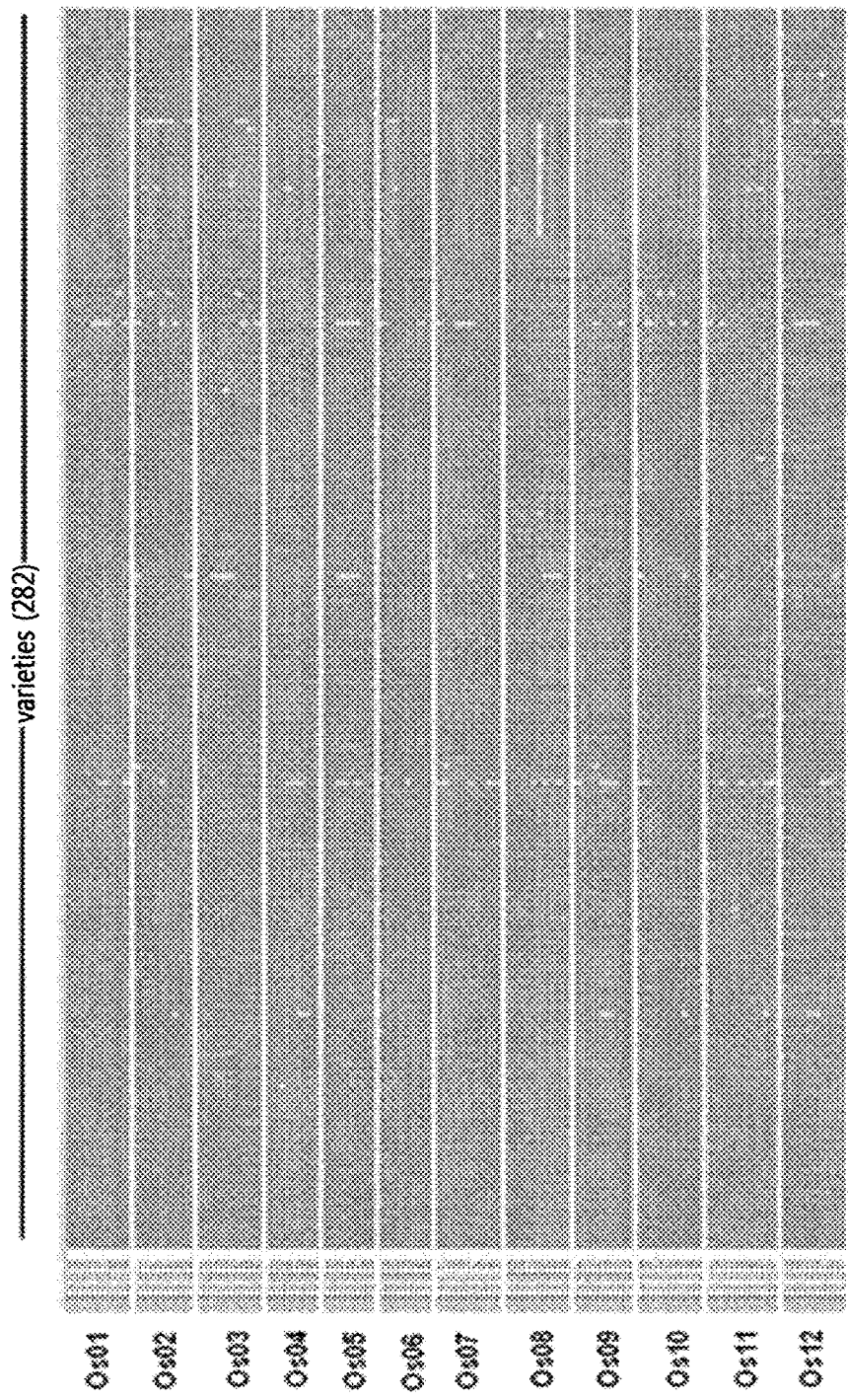

FIG. 12B is a view showing a bin map created at a chromosome level based on the identification data about 282 rice varieties constructed using the variety identification-encoding system of the present invention. Here, PCR results the same as Hwayeongbyeo and PCR results different from Hwayeongbyeo are marked with different colors, respectively.

MODE FOR INVENTION

In the present invention, the term "variation region" means a region in which a gene or a chromosome is changed, and may be represented by a dense mutation block (DMB). That is, the term "variation region" may mean a region in which genetic difference between varieties exists, and may also mean a region in single nucleotide variation (SNV) is dense. More specifically, in the present invention, when the number of single nucleotide variations (SNV), each of which is different from the reference genome in genome information, in a region is four or more per 10 kb, this region is defined as the variation region.

In the present invention, the term "single nucleotide variations (SNV)" is also referred to as "single nucleotide polymorphism (SNP)", and means the polymorphism in a single nucleotide. That is, the single nucleotide variation (SNV) is referred to as a case in which some nucleotides of the entire genome are different with respect to each chromosome. Generally, it is known that SNV exists at a rate of about one per 300 to 1000 nucleotides, but the present invention is not limited thereto.

In the present invention, the term "indel marker" is collectively referred to as a variation in which some bases are inserted into a base sequence of DNA or are deleted therefrom. The indel marker detects a region in which bases are inserted or deleted by a method of comparing and analyzing genome information about varieties used in the experiment with genome information about the reference genome, and makes a primer based on the information. Therefore, the amplification results thereof may be classified into a type of large band size (insertion) and a type of small band size (deletion), compared to those of the reference genome.

In the present invention, the term "reference genome" means a genome of a crop variety, which is a standard in the variety identification of the present invention. Preferably, in the case of bean varieties, the genome of Williams 82 may be used as the reference genome, and, in the case of rice varieties, the genome of Hwayeongbyeo may be used as the reference genome. However, the present invention is not limited thereto.

In the present invention, the term "backcross" means a process in which a plant obtained from crossing between two maternal lines is crossed with one of the maternal lines. The maternal line used in backcross is referred to as a recurrent parent line. Repetitive backcross enables a genome to have homozygosity or be inbred, and enables a genome to be similar to a recurrent parent genome.

In the present invention, the term "recurrent parent variety" means a maternal variety provided to backcross several times.

In the present invention, the term "hetero region" means a region in which a strand of maternal chromosome and a strand of paternal chromosome concurrently exist because homozygosis to a maternal line or a paternal line does not occur in the variety breeding process. As a result of amplification of a marker, when both a maternal result and a paternal result are detected in a region, this region may be defined as a hetero region.

Hereinafter, a variety identification-encoding system and an encoding method using the same according to the present invention will be described with reference to the accompanying drawings.

Figure 1:
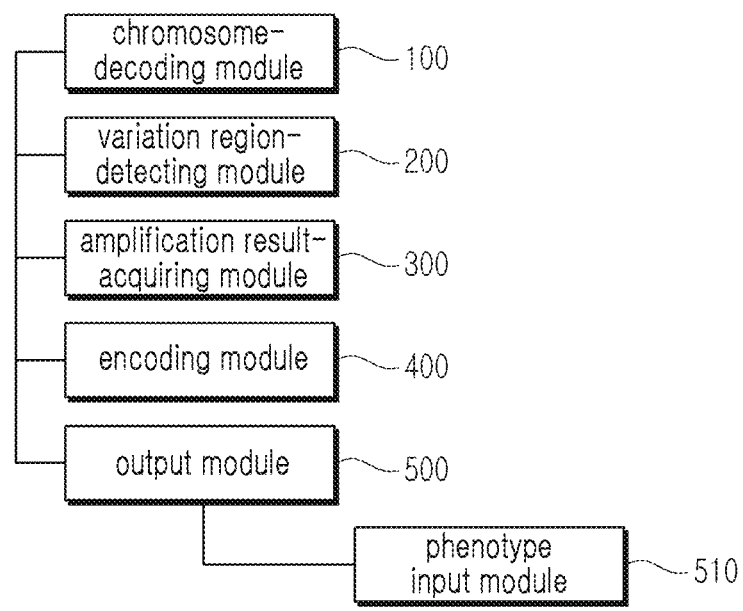
FIG. 1 is a conceptual diagram of a variety identification-encoding system according to the present invention.

First, a variety identification-encoding system according to the present invention will be schematically described with reference to FIG. 1.

The variety identification-encoding system according to the present invention includes a chromosome-decoding module 100, a variation region-detecting module 200, an amplification result-acquiring module 300, an encoding module 400, and an output module 500.

The chromosome-decoding module 100 functions to decode the chromosome of a reference genome variety and the chromosomes of target varieties. The decoding of chromosomes may be performed by a method well known in the art.

According to an embodiment of the present invention, in order to extract DNA for decoding a chromosome, 147 bean varieties (Table 1) and 282 rice varieties (Table 2) which are known in the art were respectively sown in seeding boxes for 15 days to obtain young leaves, tissues were collected from the young leaves, and DNA was respectively extracted from the tissues by the Saghai Maroof method (1984). Bean leaves frozen and stored at −70° C. were put into a mortar, and were immediately pulverized into powder while being cooled by 20 mL of nitrogen gas so as to obtain samples. 5 mL to 10 mL of cetyl trimethyl ammonium bromide (CTAB) was added to each of the samples. Then, each of the samples was more finely pulverized, put into a 25 mL centrifuge tube, and then shaken in a water tank at 60° C. for hours or more. After 10 mL of a solution of chloroform/isoamyl alcohol (24:1) was added to each of the samples, the resultant was mixed by overturning with a hand, and was then centrifugally separated at a rotation speed of 3200 rpm at 4° C. for 15 minutes so as to obtain a supernatant. The supernatant was introduced into a new tube, and 10 μL of RNase A (10 mg/mL) was added thereto. After 30 minutes, isopropanol was added to about ⅔ height of the tube to precipitate DNA so as to obtain DNA pellet. The obtained DNA pellet was taken out from the tube, added to 20 mL of ethanol and 10 mM NH$_4$OAc at 70° C., and then left overnight. Then, the DNA pellet was dried, and 1 mL of 10 mM NH$_4$OAc and 0.25 M EDTA were added thereto. The extracted DNA was confirmed in a 1% agarose gel together with λDNA, and was quantified to 20 ng/μL to be used in experiments.

Thereafter, a DNA library for DNA of each variety extracted for decoding a chromosome base sequence was created, and a base sequence of each variety was decoded according to the standard protocol in the sequencer (HiSeq2000) manufactured by Illumina Corporation. Short reads of 101 bp or 104 bp produced as a result thereof were used in bioinformatic analysis. As reference genomes for bioinformatic analysis, in the case of bean varieties, Gmax 109 soybean reference genome (Schmutz et al., 2010) was used, and, in the case of rice varieties, IRGSP build 4 rice reference genome (Goff et al., 2002) was used. The bioinformatic analysis thereof was performed using the above reference genomes by BWA algorithm (Li and Durbin, 2009) ver. 0.5.9.

TABLE 1

| No. | Variety |
|---|---|
| 1 | Nokwon |
| 2 | Dajin |
| 3 | Danmi |
| 4 | Danmi 2 |
| 5 | Mirang |
| 6 | Sangwon |
| 7 | Seokryangputkong |
| 8 | Seonnok |
| 9 | Sinrok |
| 10 | Saeol |
| 11 | Keunolkong |
| 12 | Hwaeomputkong |
| 13 | Galchae |
| 14 | Geomjeongolkong |
| 15 | Geomjeongkong 1 |
| 16 | Geomjeongkong 2 |
| 17 | Geomjeongkong 3 |
| 18 | Geomjeongkong 4 |
| 19 | Daeheuk |
| 20 | Seonheuk |
| 21 | Sohwang |
| 22 | Ilpumgeomjeong 2 |
| 23 | Jinyulkong |
| 24 | Cheongjakong |
| 25 | Cheongja 2 |
| 26 | Heukmi |
| 27 | Geumgangkong |
| 28 | Nampung |
| 29 | Dajangkong |
| 30 | Dangyeongkong |
| 31 | Danbaekkong |
| 32 | Danwonkong |
| 33 | Daemang |
| 34 | Daemang 2 |
| 35 | Daeyang |
| 36 | Daewonkong |
| 37 | Daepung |
| 38 | Daehwangkong |
| 39 | Duyukong |
| 40 | Manrikong |
| 41 | Mansu |
| 42 | Muhankong |
| 43 | Baekwoonkong |
| 44 | Bogwangkong |
| 45 | Samnamkong |
| 46 | Saealkong |
| 47 | Seonyu |
| 47 | Sodamkong |
| 49 | Songhakkong |
| 50 | Singi |
| 51 | Sinpaldalkong 2 |
| 52 | Alchankong |
| 53 | Ilmikong |
| 54 | Jangmikong |
| 55 | Jangsukong |
| 56 | Jangyeopkong |
| 57 | Jangwonkong |
| 58 | Jinmikong |
| 59 | Jinpumkong |
| 60 | Jinpumkong 2 |
| 61 | Cheongdu 1 |
| 62 | Taegwangkong |
| 63 | Hojang |
| 64 | Hwangkeumkong |
| 65 | Gwangankong |
| 66 | Namhaekong |
| 67 | Nokchae |
| 68 | Dagi |
| 69 | Dawonkong |
| 70 | Dachae |
| 71 | Doremikong |
| 72 | Myeongjunamulkong |
| 73 | Boseok |

TABLE 1-continued

| No. | Variety |
|---|---|
| 74 | Bugwangkong |
| 75 | Saebyeolkong |
| 76 | Seonamkong |
| 77 | Sogangkong |
| 78 | Sorokkong |
| 79 | Somyeongnamulkong |
| 80 | Sobaeknamulkong |
| 81 | Sowonkong |
| 82 | Sojin |
| 83 | Soho |
| 84 | Singang |
| 85 | Sinhwa |
| 86 | Anpyeong |
| 87 | Wongwang |
| 88 | Wonhwang |
| 89 | Eunhakong |
| 90 | Iksannamulkong |
| 91 | Janggi |
| 92 | Jonam |
| 93 | Paldonamulkong |
| 94 | Pureunkong |
| 95 | Pungsannaumlkong |
| 96 | Pungwon |
| 97 | Hannamkong |
| 98 | Hoseo |
| 99 | Geomjeongsaeol |
| 100 | Cheongja 3 |
| 101 | Gwanggyo |
| 102 | Daol |
| 103 | Deokyu |
| 104 | Sinpaldalkong |
| 105 | Paldalkong |
| 106 | Hwasungoputkong |
| 107 | Heukcheong |
| 108 | Seoritae |
| 109 | Seomoktae |
| 110 | Orialtae |
| 111 | Hanagari |
| 112 | Jangdanbaekmok |
| 113 | Geumgangsorip |
| 114 | Chungbukbaek |
| 115 | Gwangdu |
| 116 | Baekcheon |
| 117 | Saedanbaekkong |
| 118 | Sowon 2010 |
| 119 | Ilpumgeomjeong |
| 120 | Hanoi |
| 121 | Socheong 2 |
| 122 | Daeha |
| 123 | Daeha 1 |
| 124 | Wooram |
| 125 | Hwangkeumol |
| 126 | Geomjeong 5 |
| 127 | Cheonsang |
| 128 | Heukseong |
| 129 | Joyang 1 |
| 130 | Cheongyeop 1 |
| 131 | Chamol |
| 132 | Jungmo 3005 |
| 133 | Jungmo 3006 |
| 134 | Jungmo 3007 |
| 135 | Neulchan |
| 136 | Wonheuk |
| 137 | Galmi |
| 138 | Jungmo 3003 |
| 139 | Jungmo 3004 |
| 140 | Jungmo 3002 |
| 141 | Socheong |
| 142 | Hoban |
| 143 | Enrei |
| 144 | PI96983 |
| 145 | L29 |
| 146 | V94-5152 |
| 147 | L68 |
| Total | 147 varieties |

TABLE 2

| Group | Varieties | Number of varieties |
|---|---|---|
| G1 | Jinbueul, jukjinjuchal, Sobak, Keumo, Odae, wolbak, Dunae, Woonbong, Woonjang, Samcheon, Jinbong, Woonmi, Inwol, Obong, Jukjinju, hwangkeumbora, Daejin, Manna, Hwadong, Geuroo, Sinwoonbong 1, Sangju, Munjang, Jinmi, Gunyangmi, Daechan, Joeunheukmi, Josaengheukchal, Woonkwang, Jungmo 1011, Woondoo, Sangjuchal, Sinbaek, Jinbuchal, Cheongbaekchal | 35 |
| G2 | Hanseol, Kowoon, Taesung, Taebong, Jinbu, Joan, Odae 1, Hoban, Junghwa, Sura, Ansung, Seoan, Gangbaek, Geuman, Pungmi, Jungsaenggold, Matdream, Jungmo 1017, Oryun, Manjong, Cheonga, Boseok, Juan, Hongjinju, Gopum, Joryeong, Mipum, Dongjinchal, Saenuri, Saesangju, Naepung, Manchu, Joabi, Sambaek, Sandeuljinmi, Jungmo 1007, Jungmo 1012, Jungsan, Handeul, Sangmi, Seolaemi, Jokwang | 42 |
| G3 | Heukjinju, Heukseol, Jopyeong, Seonhyangheukkmi, Heukgwang, Seolbaeg, Goami 3, Ilpum, Seolgang, Goami 4, Goami 2, Baekjinju, Cheongcheongjinmi, Baekjinju, Jungmo 1003, | 15 |
| G4 | Pyeongwon, Ansan, Jungmo 1001 | 3 |
| G5 | Keumohbyeo 3, Cheongnam, Namwon, Jungan, Gangchan, Sinwoonbong, Jungmo 1010, Gancheok, Seoan 1, Keumohbyeo 2, Cheongan, Anjung, Hwaan, Sampyeong, Danmi, Seokjeong, Seojin, Bongkwang, Nunbora, Seolhyangchal, Hwaseonchal, Sinseonchal, Borami, Donghae, Aranghyangchal, Boseokheukchal, Hwajin, Hwamyeong, Daean, Geumnam, Hopyeong, Yangjo, Cheonghaejinmi, Keumohbyeo 1, Hyangnam, Mihyang, Manho, Hwajung, Manpung, Nakdong, Jungmo 1006, Mangeum, Hwashin, Manan, Nampyeong, Heukhyang, Hwashin 1, Cheongho, Jungmo 1004, Pungmi 1, Jungmo 1016, Jowoon, Saechoocheong, Choocheong, Tamjin | 55 |
| G6 | Heuknam, Sintoheukmi, Sinmyeongheukchal, Sinnongheukchal | 4 |
| G7 | Jinpum, Daepyeong, Cheongmyeong | 3 |
| G8 | Joonamjosaeng, Jangahn, Saeilmi, Jongnam, yeongahn, Hwabong, Honong, Saegoami, Yeongnam, Wonhwang, Namgang, Dongjin, Jinbaek, Dongahn, Daesan, Goami, Baekokchal, Hwanam, Hoahn, Hwarang, Manmi, Hwaseong, Haeoreumi, Daecheong, Gyehwa, Haiami, Nongho, Migwang, Geonganghongmi | 31 |
| G9 | Cheongdam, Namil, Daeripbyeo 1 | 3 |
| G10 | Sooahn, Haepyeong, Palgong, Suryeojinmi, Sangok, Yeonghae, Hwayeong, Dongbo, Seopyeong, Segyehwa, Dongjin 1, Manwol, Chinnong, Sugwang, Onnuri, Jungmo 1013, Daebo, Hopum, Donghaejinmi, Dongjin 2, Junam, Anmi, Hanam, Jungmo 1005, Dacheong, Heemangchan, Hanmaeum, Pyeongan, Dami, Sindongjin, Hwangkeumnodeul, Boramchan, Deuraechan, Samgwang, Jungmo 1014, Hwasam, Hwangkeumnuri, Jinsumi, Samdeok, Boseokchal, Jungmo 1015, Haepyeongchal, Malgeumi, Sobi, Sodami, Baekseolchal, Jungmo 1008, Haechanmulgyeol, Seogan, Hojin, Jungmo 1002, Keunoon, Sujin, Jinbo, Chilbo, Yeonghojinmi, Seomyeong | 58 |

TABLE 2-continued

| Group | Varieties | Number of varieties |
|---|---|---|
| G11 | Sangnambat, Mokyang | 2 |
| G12 | Nongan, Namcheon, Milyang 23, Areum, Namyoung, Taebag, Segyejinmi, Nampung, Jungwon, Jangsung, Cheongcheong, Milyang 29, Anda, Dasan 2, Dasan, Dasan 1, Keunsum, Hanareum, Hanareum 2, Gaya, Yongmun, Samgang, Hangangchal, Hanganchal 1, Pungsan, Hyangmibyeo 2, Hyangmibyeo 1, Chilsung, Mokwoo, Nokyang | 31 |
| Total | 12 groups, 282 varieties | 282 |

The variation region-detecting module 200 detects variation regions from the decoded chromosome through single nucleotide variation (SNV) dense region analysis. In the detection of the variation region, single nucleotide variations (SNV) are detected while comparing base sequence information of varieties to be analyzed with that of the reference genome. In this case, when the number of single nucleotide variations (SNV) showing a difference between the base sequence information and the genome information of the reference genome is four or more per 10 kb, in the present invention, this variation region is referred to as a dense mutation block (DMB).

Specifically, when another variation region adjacent to any variation region is present within an interval of 90 kb, these variation regions may be combined into one variation region. Further, regions other than variation regions are represented by common regions, and when an adjacent common region is present within an interval of 30 kb, this common region may be represented by the same region. For the visualization of the above contents, in the display on a chromosome, DMB may be marked by gray boxes, and common regions may be marked with white. However, the present invention is not limited thereto.

Figure 4A:
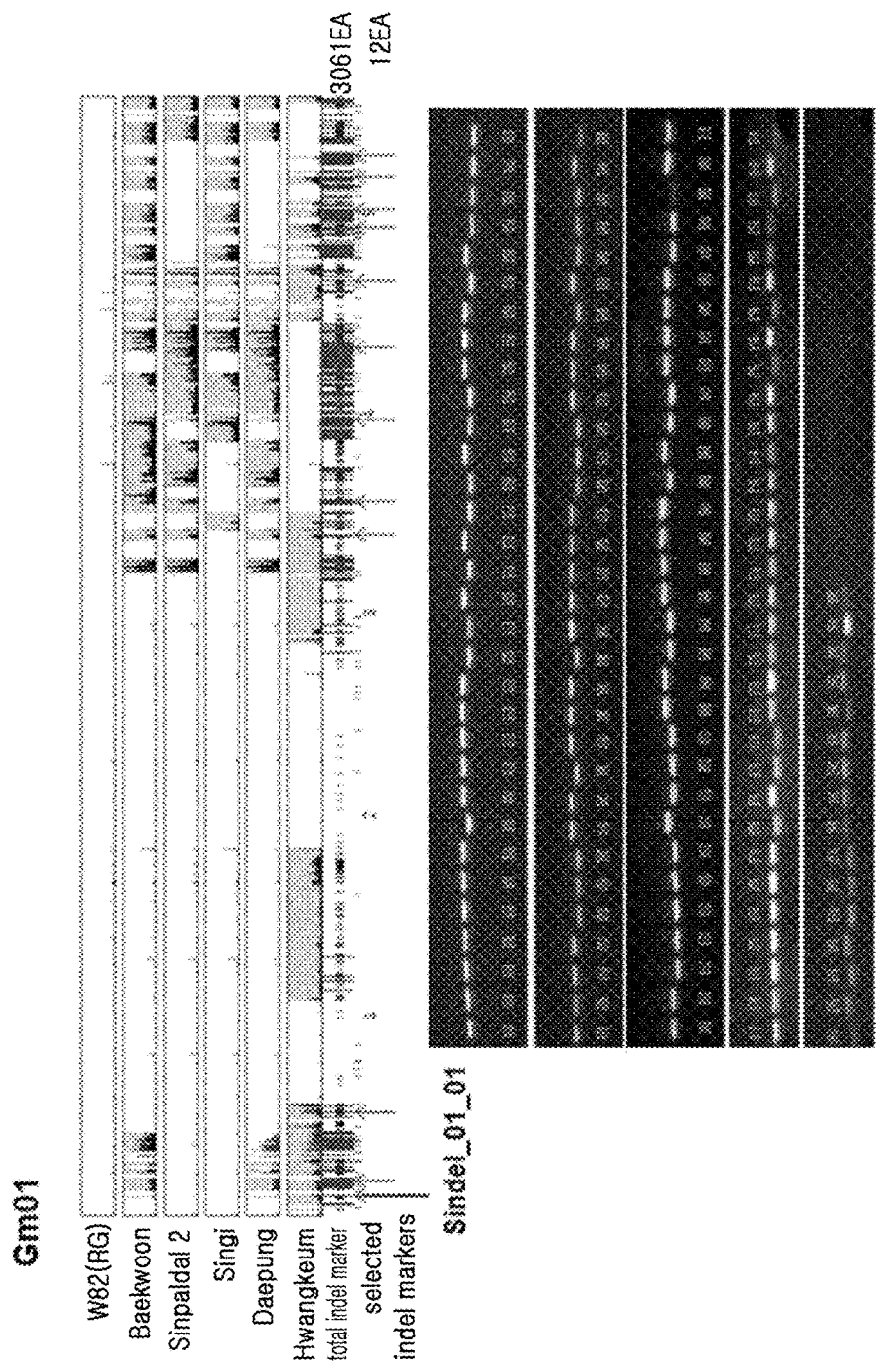
FIG. 4A is a view showing the results of PCR amplification of 3,061 variation region (DMB)-specific indel markers developed by decoding chromosome 1 of six kinds of bean varieties.
Figure 4B:
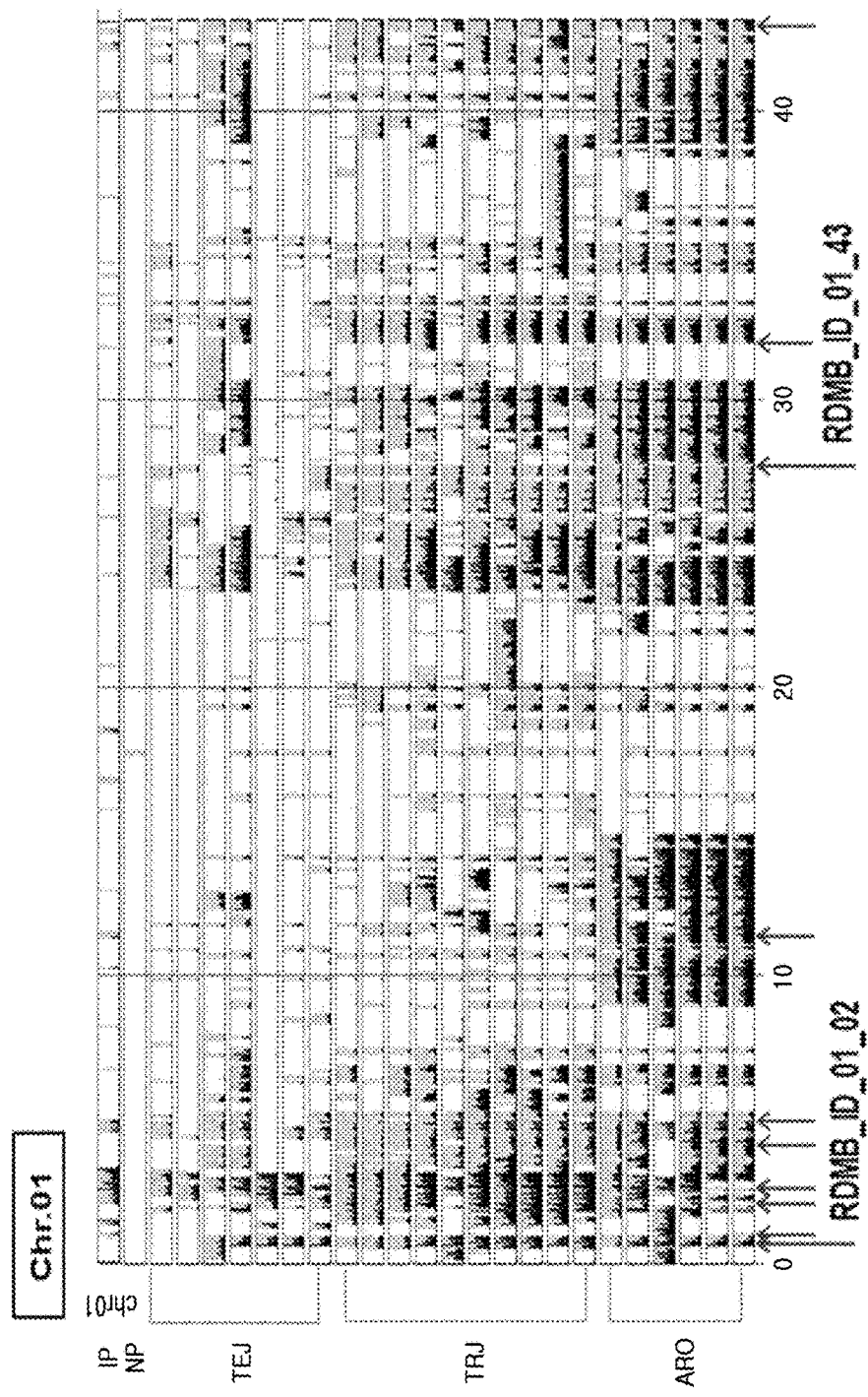
FIG. 4B is a view showing variation region (DMB)-specific indel markers (arrows) developed by decoding chromosome 1 of six kinds of bean varieties. Here, IP means Ilpum rice, NP means Nippon Barre (reference genome), TEJ means temperate rice, TRJ means tropical rice, and ARO means flavor rice.
Figure 4C:
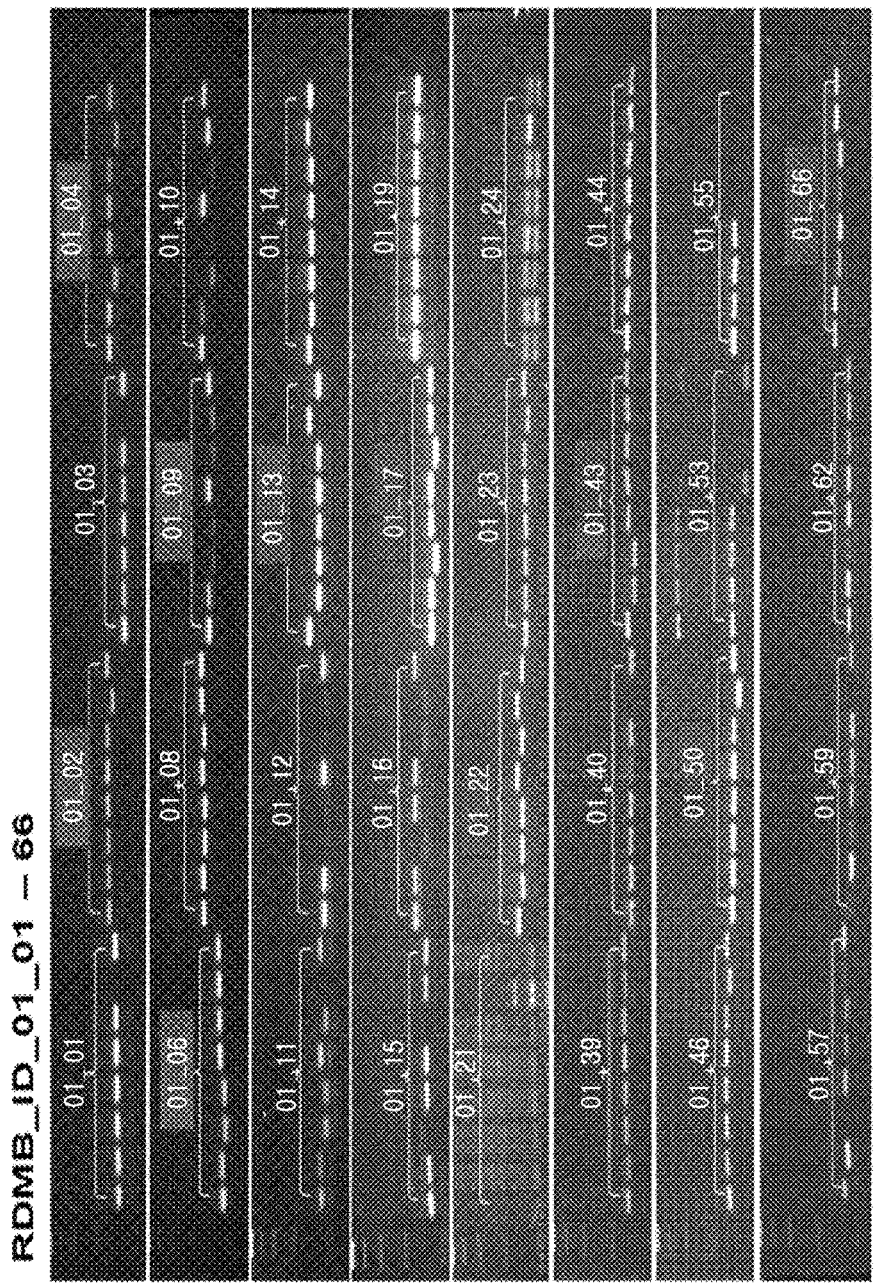
FIG. 4C is a view showing the results of PCR amplification of variation region (DMB)-specific indel markers developed by decoding chromosome 1 of rice varieties. 66 kinds of primarily selected markers were tested for eight kinds of rice varieties, and then ten kinds of markers representing excellent PCR results were selected.

Specifically, according to an embodiment of the present invention, for the detection of variation regions in genomes of bean varieties, the full-length genomes of five bean varieties of Baekwoonkong, Sinpaldalkong 2, Daepung, and Hwangkeumkong, and the full-length genome of Williams 82, which is a reference genome, were decoded. As a result of detecting variation regions through single nucleotide variation (SNV) dense region analysis based on the decoded genome information, when 20 chromosomes were analyzed, all 2,274 variation regions were detected, and, for each chromosome, 161 variation regions (most regions) were detected in chromosome 3, whereas 65 variation regions (fewest regions) were detected in chromosome 14 (Table 3). Among these, in the case of chromosome 1, it was ascertained that 112 variation regions were detected by decoding six bean varieties (FIG. 4A).

Further, for the detection of variation regions in genomes of rice varieties, the full-length genomes of 24 rice varieties including Ilpum rice, temperate rice, tropical rice, and flavor rice, and the full-length genome of Nippon Barre, which is a reference genome, were decoded. As a result of detecting variation regions through single nucleotide variation (SNV) dense region analysis based on the decoded genome information, when twelve chromosomes were analyzed, all 2,797 variation regions were detected, and, for each chromosome, 335 variation regions (most regions) were detected in chromosome 1, whereas 181 variation regions (fewest regions) were detected in chromosome 10 (Table 4).

The amplification result-acquiring module 300 functions to acquire amplification results by setting indel markers in the detected variation regions and amplifying the set indel markers with PCR.

According to an embodiment of the present invention, in order to select variation region-specific indel markers, indel markers were designed using a Primer 3 program based on the above-analyzed base sequences, and the expected sizes of amplification products were set to 100 bp to 150 bp. The amount of a mixture (master mix) of a PCR reaction was set to 10 µL, and the mixture was configured to include 20 ng of genomic DNA, 0.4 pmol of each primer, and 5 µL of GoTaq Green Master Mix (Promega, Madison, Wis., USA). In the PCR amplification, initial denaturation was performed at 95° C. for 5 minutes using a Biometra thermocycler (Biometra, Gottingen, Germany), secondary denaturation was performed at 95° C. for 30 seconds, annealing was performed at 48° C. for 30 seconds, amplification was repeatedly performed at 72° C. for 30 seconds during a total of 34 cycles, final amplification was performed at 72° C. for 10 minutes, and then the PCR amplification reaction was completed at 4° C. The amplified PCR product was loaded in an agarose gel, and was then electrophoresed at a voltage of 150 V for 60 minutes to 80 minutes. After the electrophoresis, the PCR product was dyed with ethidium bromide (EtBr), and then bands were observed using UV.

In order to select the variation region-specific indel markers of bean varieties through the above processes, 73,327 markers were initially designed based on the genome-decoding information. Based on this information, for each chromosome, 20 indel marker primers were made, and 202 markers having characteristics of indel markers in which two types of bands are accurately amplified were selected (Table 3). As a result, the number of selected markers for each chromosome was distributed in a range of eight to twelve, and the PIC average value of selected markers was 0.38 (Table 3).

TABLE 3

| Chromosome No. | Number of DMBs | Number of designed indel markers | Number of selected indel markers | Number of analyzed indel markers | PIC values of indel markers |
|---|---|---|---|---|---|
| Gm01 | 112 | 3,061 | 20 | 12 | 0.39 |
| Gm02 | 123 | 3,466 | 20 | 12 | 0.40 |
| Gm03 | 161 | 4,744 | 20 | 12 | 0.42 |
| Gm04 | 113 | 3,336 | 20 | 11 | 0.42 |
| Gm05 | 106 | 2,939 | 20 | 12 | 0.41 |
| Gm06 | 121 | 3,525 | 20 | 9 | 0.41 |
| Gm07 | 144 | 3,444 | 20 | 8 | 0.43 |
| Gm08 | 126 | 3,047 | 20 | 10 | 0.42 |
| Gm09 | 124 | 4,430 | 20 | 11 | 0.36 |
| Gm10 | 136 | 2,979 | 20 | 9 | 0.36 |
| Gm11 | 111 | 2,126 | 20 | 10 | 0.36 |
| Gm12 | 119 | 2,781 | 20 | 8 | 0.38 |
| Gm13 | 111 | 4,102 | 20 | 9 | 0.41 |
| Gm14 | 65 | 4,217 | 20 | 11 | 0.30 |
| Gm15 | 84 | 4,572 | 20 | 10 | 0.39 |
| Gm16 | 73 | 4,281 | 20 | 8 | 0.39 |
| Gm17 | 116 | 3,161 | 20 | 12 | 0.37 |
| Gm18 | 100 | 6,751 | 20 | 10 | 0.36 |
| Gm19 | 118 | 3,894 | 20 | 10 | 0.34 |
| Gm20 | 111 | 2,471 | 20 | 8 | 0.36 |
| Total | 2,274 | 73,327 | 400 | 202 | 0.38 |

Further, in order to select the variation region-specific indel markers of rice varieties, 12,174 markers were initially designed based on the genome-decoding information. Among these, 20 indel marker primers representing variety-specific variation regions were made, and 112 markers having characteristics of indel markers in which two types of bands are accurately amplified were selected (Table 4). As a result, the number of selected markers for each chromosome was distributed in a range of eight to ten, and the PIC average value of selected markers was 0.37 (Table 4).

TABLE 4

| Chromosome No. | Number of DMBs | Number of designed indel markers | Number of selected indel markers | Number of analyzed indel markers | PIC values of indel markers |
| --- | --- | --- | --- | --- | --- |
| Chr. 01 | 335 | 1,330 | 66 | 10 | 0.41 |
| Chr. 02 | 311 | 1,047 | 56 | 9 | 0.33 |
| Chr. 03 | 225 | 596 | 55 | 10 | 0.40 |
| Chr. 04 | 276 | 1,143 | 56 | 8 | 0.40 |
| Chr. 05 | 196 | 606 | 42 | 8 | 0.35 |
| Chr. 06 | 205 | 1,042 | 46 | 8 | 0.36 |
| Chr. 07 | 233 | 1,213 | 52 | 10 | 0.37 |
| Chr. 08 | 211 | 1,090 | 46 | 10 | 0.20 |
| Chr. 09 | 182 | 673 | 40 | 9 | 0.40 |
| Chr. 10 | 181 | 1,169 | 40 | 10 | 0.32 |
| Chr. 11 | 253 | 1,368 | 56 | 10 | 0.45 |
| Chr. 12 | 189 | 897 | 40 | 10 | 0.44 |
| Total | 2,797 | 12,174 | 595 | 112 | 0.37 |

Meanwhile, the amplification result-acquiring module 300 acquires the amplification result as "a" when the band size of an amplification result of a reference genome variety is the same as the band size of an amplification result of a target variety, and acquires the amplification result as "b" when the band size of the amplification result of a reference genome variety is different from the band size of the amplification result of a target variety. Here, the amplification results are limited to "a" or "b" as long as they are different from each other according to the band size.

Thereafter, the encoding module 400 functions to encode the amplification results thereof.

Specifically, the encoding module 400 converts the amplification result "a" into a digital signal "0" to be marked with white, and converts the amplification result "b" into a digital signal "1" to be marked with black. The encoding module 400 can create a barcode using the white and black marks. Further, the encoding module 400 marks the digital signal "0" with white, and marks the digital signal "1" with black. However, the color thereof is not limited.

The barcode may be selected from a one-dimensional expression and a two-dimensional expression.

Figure 6A:
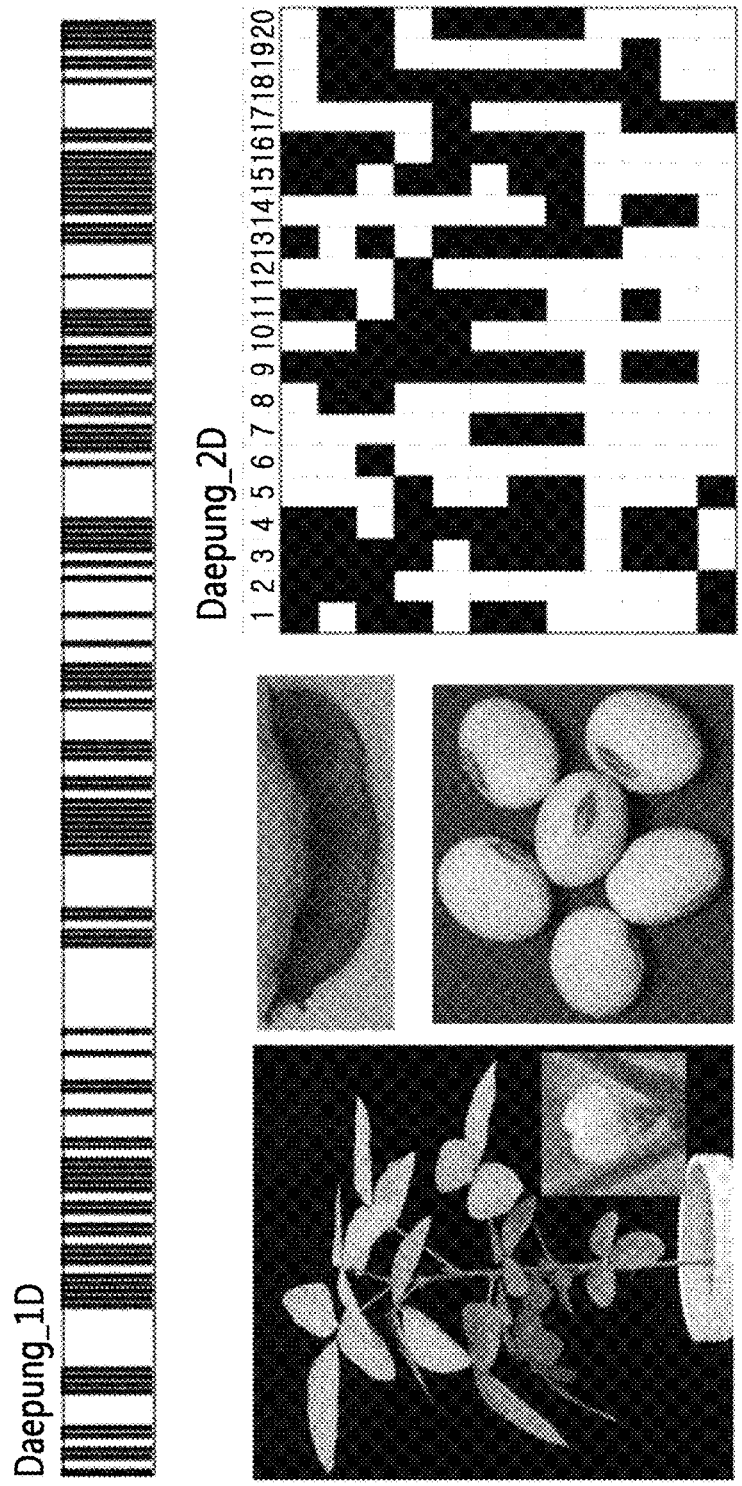
FIG. 6A is a view showing the one-dimensional encoding and two-dimensional encoding of bean variety "Daepung".
Figure 6B:
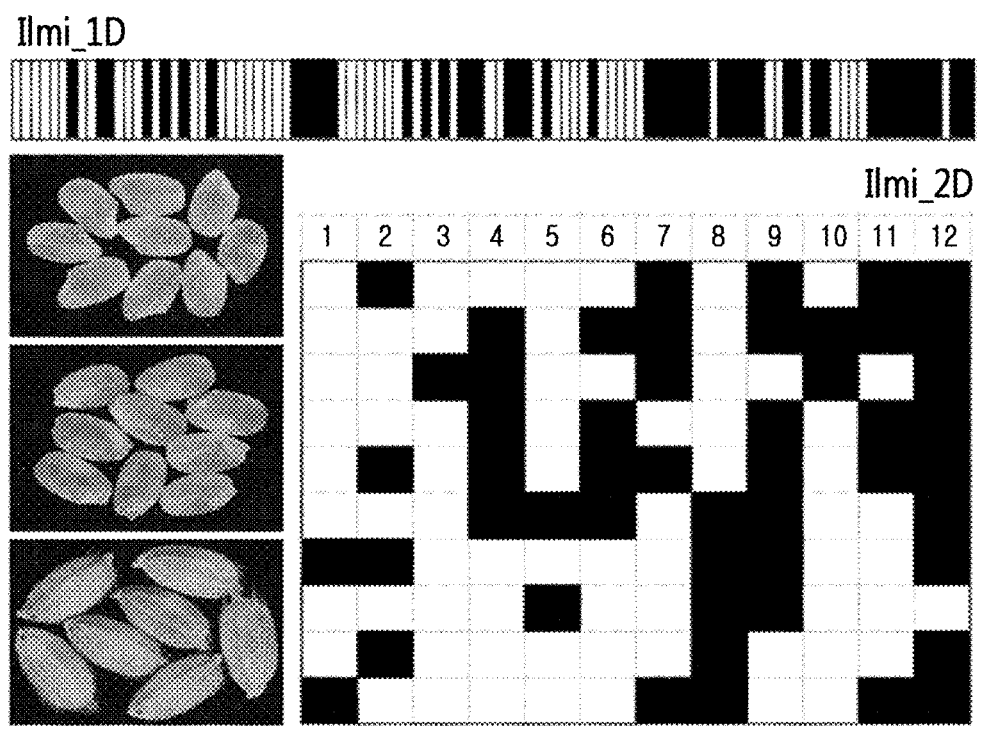
FIG. 6B is a view showing the one-dimensional encoding and two-dimensional encoding of rice variety "Ilmi".

Examples of one-dimensionally expressed barcodes are shown in FIGS. 6A and 6B. The barcode is created by linearly connecting chromosomes 1 to n. Examples of two-dimensionally expressed barcodes are also shown in FIGS. 6A and 6B. The two-dimensionally expressed barcode is advantageous in that a DMB-specific pattern for each chromosome can be easily understood at a glance.

The variety identification-encoding system according to another embodiment of the present invention may include a phenotype input module 510 receiving a phenotype of a target variety and transmitting the phenotype thereof to the output module 500. The phenotype, such as plant type, flower color, seed shape, belly color, or the like, of each variety can be inputted to the phenotype input module 510. The phenotype thereof is not limited thereto. Thus, since both a name and phenotype of the variety are represented, the characteristics of the variety can be understood at a glance.

Meanwhile, the output module 500 can output two or more encoded results.

Figure 7A:
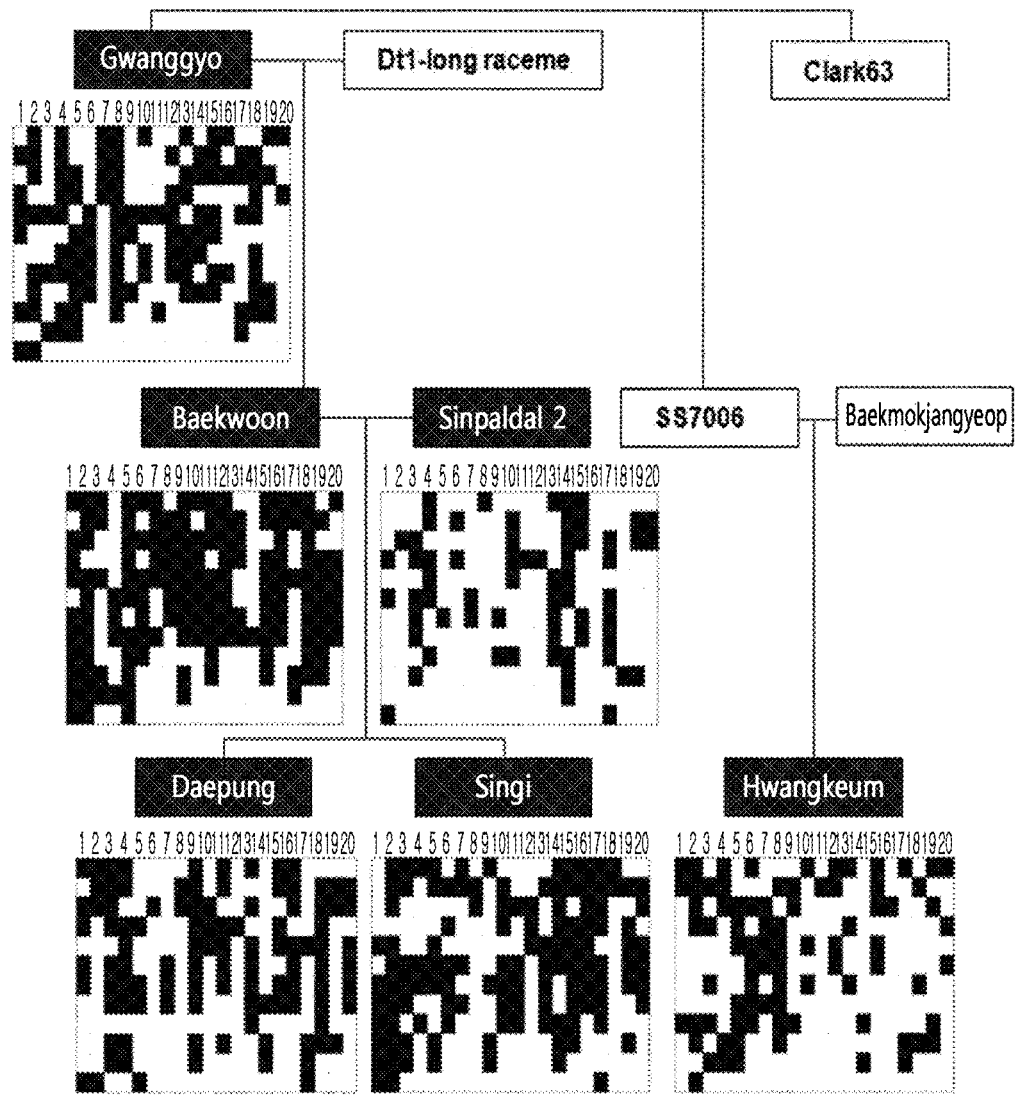
FIG. 7A is a view showing an example in which the variety identification-encoding system of the present invention is applied to a bean variety breeding lineage tree.
Figure 7B:
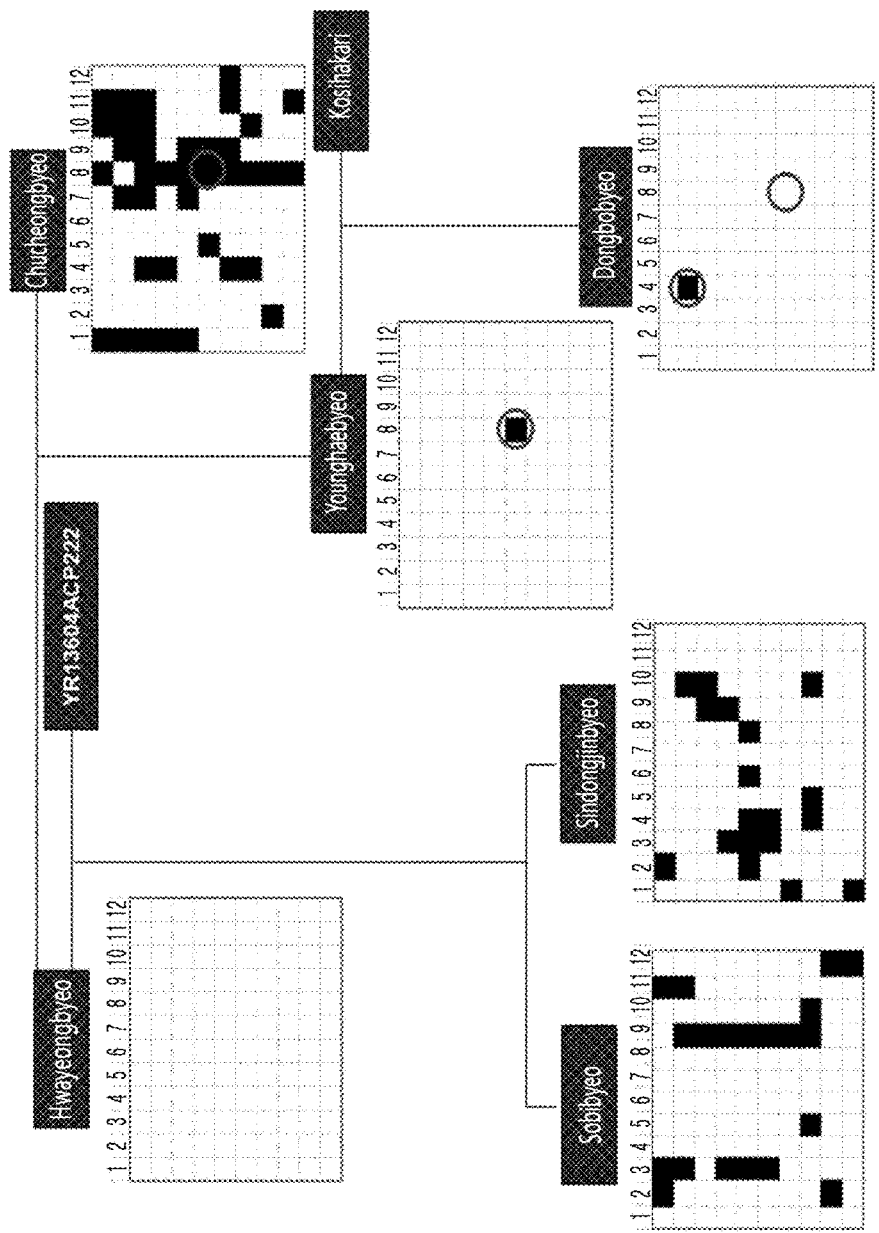
FIG. 7B is a view showing an example in which the variety identification-encoding system of the present invention is applied to a rice variety breeding lineage tree.

For example, as shown in FIGS. 7A and 7B, two or more encoded results are outputted by a two-dimensional expression, but information about female or male varieties may also be outputted as a linage tree.

Since each variety has its own specific variation region (DMB) pattern, it is clearly distinguished from other varieties. Therefore, the variety identification-encoding system of the present invention can be easily used to identify varieties.

According to an embodiment of the present invention, when the system of the present was applied to two varieties of Daepung and Singi bred by using Baekwoonkong as a female variety and using Sinpaldalkong as a male variety, it was found that whether the variation region (DMB) for each chromosome is derived from the female variety or the male variety can be accurately detected. Specifically, when chromosome 1 was used as a target, in the case of Singi, the specific variation region (DMB) of the front portion thereof was derived from Sinpaldalkong 2, and the specific variation region (DMB) of the back portion thereof was derived from Baekwoonkong, whereas, in the case of Daepung, it tends to show a result opposite to Singi, and thus it can be ascertained that recombinations occur more frequently (FIG. 7B).

Further, when the system of the present was applied to two varieties of Sobibyeo and Sindonjinbyeo bred by using Hwayeongbyeo as a female variety and using YR1360ACP222 as a male variety, it could be accurately detected whether the variation region (DMB) for each chromosome is derived from the female variety or the male variety. Specifically, it can be seen from the lineage tree of FIG. 7B that black regions were derived from the male variety even though there is no data about the male variety.

For another example, the output module 500 outputs two or more encoded results by a two-dimensional expressions, but can automatically or manually detect the differences between the two or more two-dimensional expressions and mark these differences with colors other than white and black.

Further, the variety identification-encoding system of the present invention can be applied to the identification of varieties bred by backcross. The identification of varieties using conventional molecular markers has a limitation in that the variety bred by backcross has very high genetic similarity to the variety used as recurrent parent, and thus it is difficult to distinguish these two varieties.

Figure 8A:
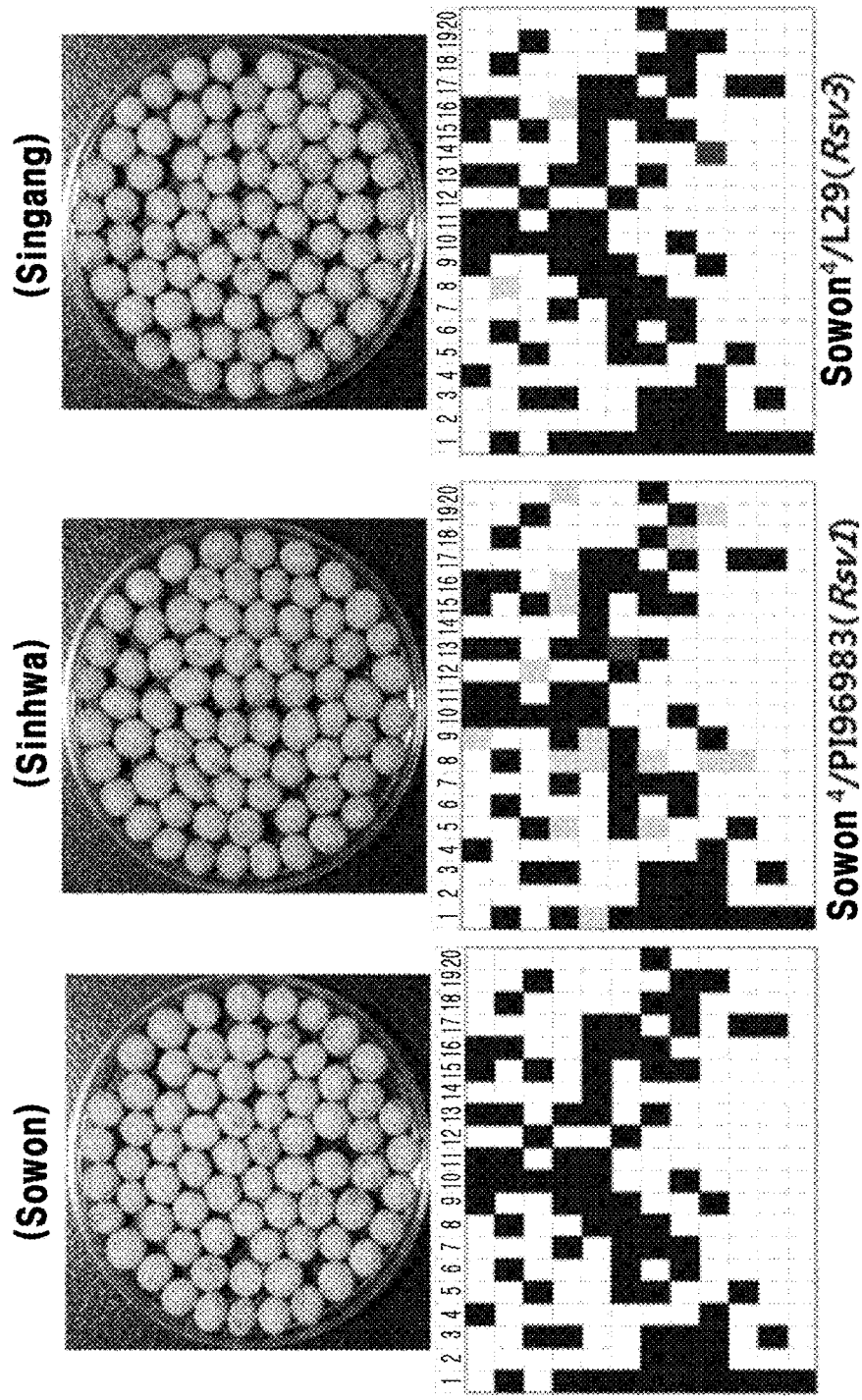
FIG. 8A is a view comparing bean varieties bred by backcross with recurrent parent bean varieties using the variety identification-encoding system of the present invention. Here, regions the same as Williams 82 are marked with white, regions different from Williams 82 are marked with black, and introduced locus regions and regions different from recurrent parent bean varieties are marked with colors other than white and black.

According to an embodiment of the present invention, when the encoding system of the present invention was applied to Sinhwa, which is bred to introduce $R_{SV}1$ (soybean mosaic virus (SMV)-resistant gene) into Sowonkong, Singang, into which $R_{SV}3$ is introduced, and Sowonkong, which is used as recurrent parent, the two varieties of Sinhwa and Singang had very high genetic similarity to Sowonkong, but each of the varieties can be accurately distinguished by their own specific variation region (DMB) patterns (FIG. 8A).

Further, DMB, at which a transgene locus is placed, can be detected automatically or manually. As shown in FIG. 8 in which DMB is marked with colors other than white and black, the above DMB and other DMBs not completely replaced by Sowonkong are accurately detected as in the drawing. Therefore, it was ascertained that this system can be effectively used in backcross-bred recurrent parent gene selection (background selection) (FIG. 8A).

Figure 8B:
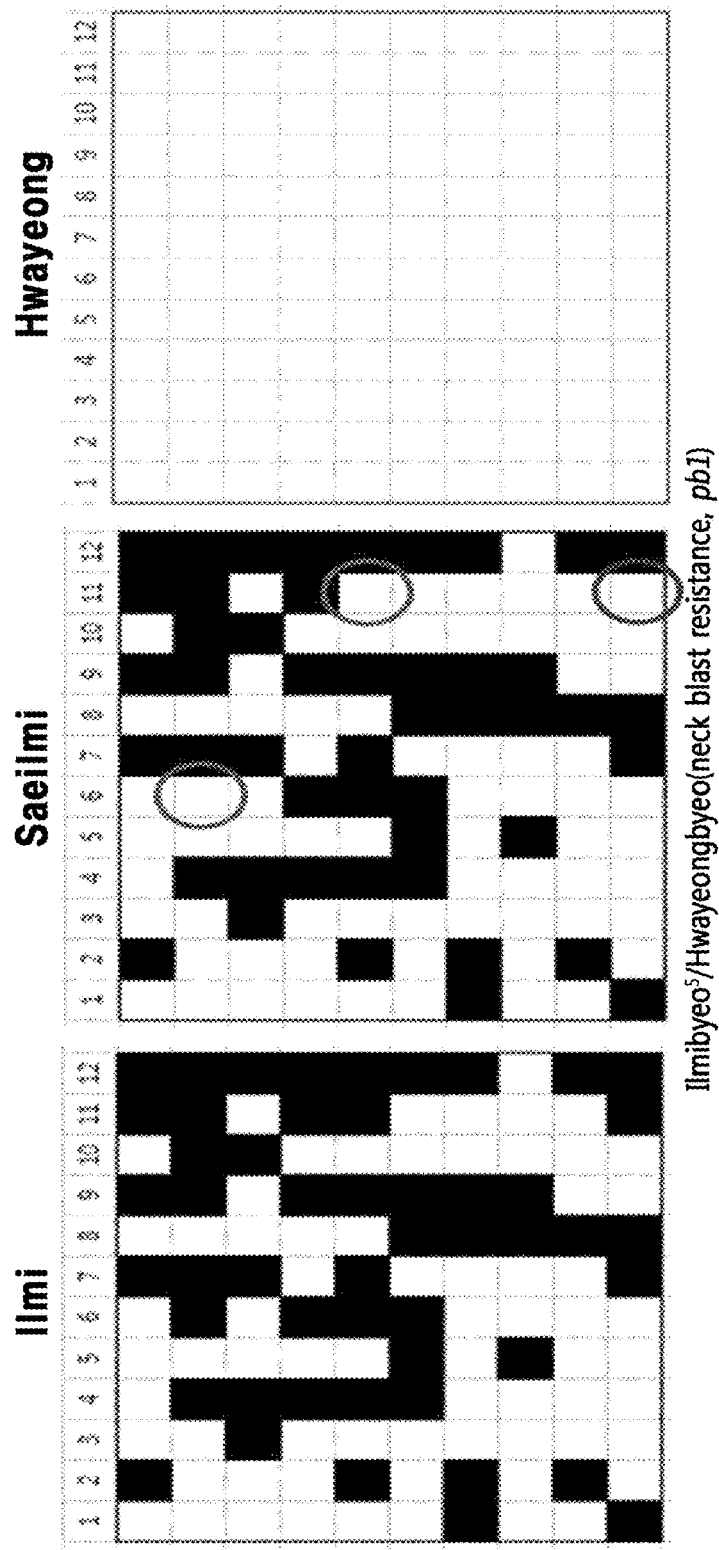
FIG. 8B is a view comparing rice varieties (New Ilmi) bred by backcross with recurrent parent rice varieties using the variety identification-encoding system of the present invention. Here, regions the same as Hwayeongbyeo are marked with white, regions different from Hwayeongbyeo are marked with black, and introduced locus regions and regions different from recurrent parent rice varieties are marked with circles.

Meanwhile, as a result of applying the variety identification-encoding system of the present invention to rice varieties developed by backcross breeding, it was ascertained that two varieties (Ilmi and Saeilmi) having high genetic similarity can be clearly distinguished, and transgene regions and regions not completely replaced by recurrent parent varieties can also be detected (FIG. 8B).

Figure 9:
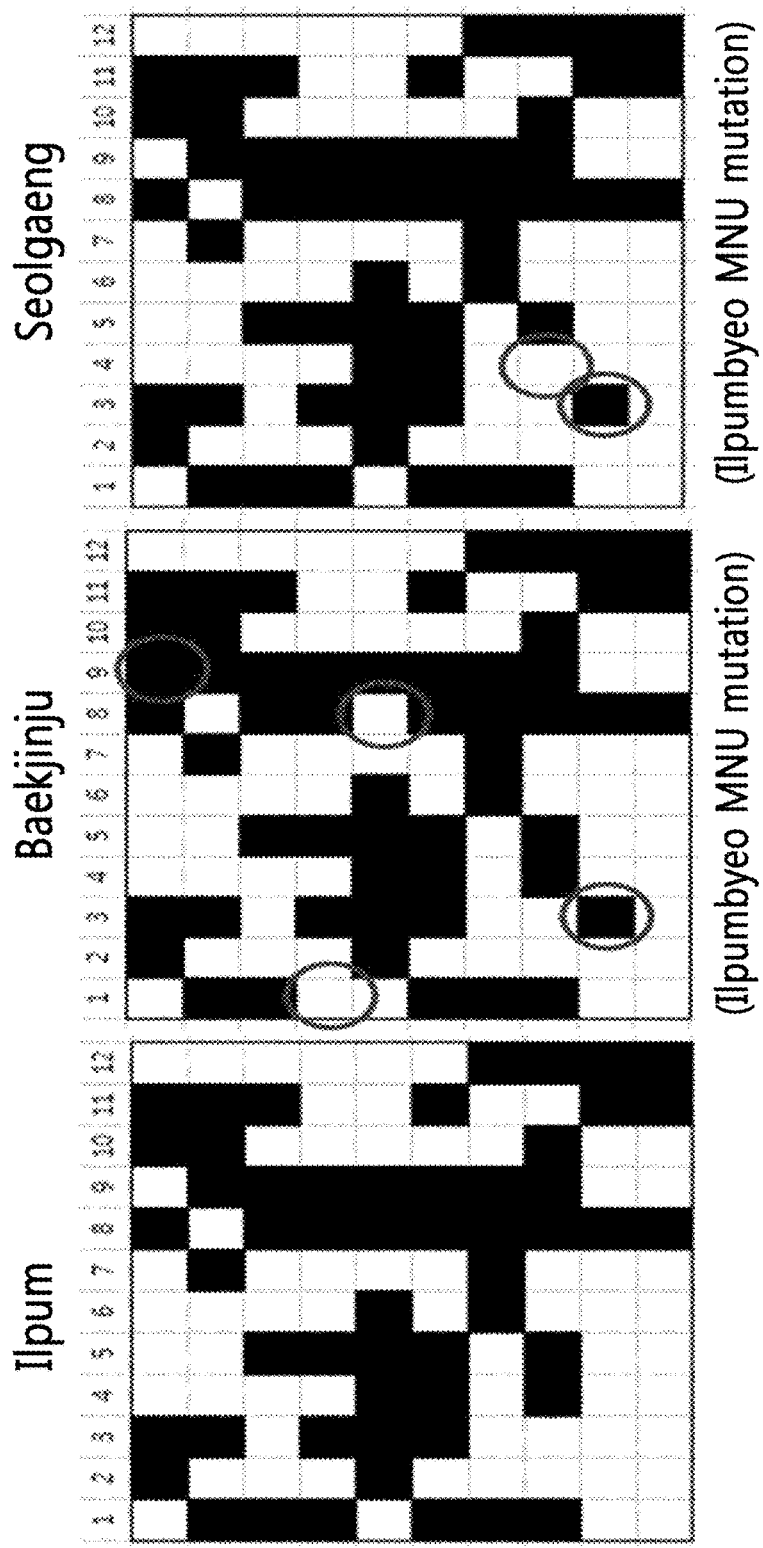
FIG. 9 is a view showing an example in which the variety identification-encoding system of the present invention is applied to mutant varieties. Here, regions the same as Hwayeongbyeo are marked with white, regions different from Hwayeongbyeo are marked with black, and regions different from Ilpumbyeo are marked with circles.

Further, the variety identification-encoding system of the present invention can be applied to the identification of mutant varieties (FIG. 9).

According to an embodiment of the present invention, as a result of applying the variety identification-encoding system of the present invention to Baekjinju and Seolgang, which was bred by treating Iipum rice with N-methyl-N-nitrosourea (MNU), which is a mutant-inducing source, it was ascertained that regions different from those of Ilpumbyeo were accurately detected in both of the two varieties. Specifically, it was examined that one of chromosomes 1, 3, 8, and 9 in Baekjinju is different from that in Ilpum, and one of chromosomes 3 and 4 in Seolgang is different from that in Ilpum.

Further, in order to measure the accuracy of the variety identification-encoding system of the present invention, 282 rice varieties were classified into twelve groups at a genetic similarity of 0.68 (Table 2 and FIG. 10A). Among these groups, as a result of applying the system of the present invention to target varieties having high genetic similarity in Group 10 (G10), even in the case of Dongbo and Younghae having a genetic similarity of 0.997, each position (one of chromosomes 4 and 8) different from that in Hwayeongbyeo was accurately detected, thereby ascertaining the fact that the variety identification ability of the system of the present invention is very accurate (FIGS. 10A and 10C). Similarly, even when the system of the present invention was applied to target varieties having high genetic similarity in Group 12 (G12), it was ascertained that positions having differences among three varieties of Jungwon, Jangsung, and Cheongcheong, three varieties of Keunsum, Hanareum, and Hanareum 2, and three varieties of Gaya, Yongmun, and Samgang, having high genetic similarity, were accurately detected (FIG. 11A).

This suggests that the variety identification-encoding system of the present invention can be effectively used even in the identification of varieties having high genetic similarity to the original variety.

For still another example, as shown in FIGS. 11A and 11B, the output module 500 outputs two or more encoded results by a two-dimensional expression, but can automatically or manually detect hetero regions and mark these hetero regions with colors other than white and black.

Specifically, the variety identification-encoding system of the present invention can be applied in order to investigate the degree of immobilization of varieties.

In the case of crops including beans whose varieties are developed by cross-breeding, the immobilization of breeding lines corresponds to a very important factor for uniformity and stability of varieties.

According to an embodiment of the present invention, when the variety identification-encoding system of the present invention was applied to 147 varieties, it was ascertained that Cheongjakong (three regions of chromosome 14) and Pungwonkong (one region of each of chromosomes 3, 4, 10, and 13) were not completely immobilized because hetero regions were marked with colors other than white and black (FIG. 11A).

Further, the variety identification-encoding system of the present invention can be applied to the rapid immobilization of separating and breeding lines because it can accurately detect whether any region of any chromosome is a hetero region. Specifically, as shown in FIG. 11B, the RDM-B_ID_08_20 marker of chromosome 8 can be usefully used to identify uniform-type rice varieties because the occurrence of specific heterogeneous reactions in the uniform-type rice varieties can be represented by this marker (FIG. 11B).

Furthermore, a chromosome map (bin map) can be created at a chromosome level using the variety identification-encoding system of the present invention (FIGS. 12A and 12B). Due to the creation of the chromosome map (bin map) at a chromosome level, the analyses of similarity between varieties, population structures, and the like can be effectively performed, and the change of a variation region (DMB) at a chromosome level can be quickly detected because the investigation of recombination patterns of newly-breeding varieties becomes possible.

Figure 2:
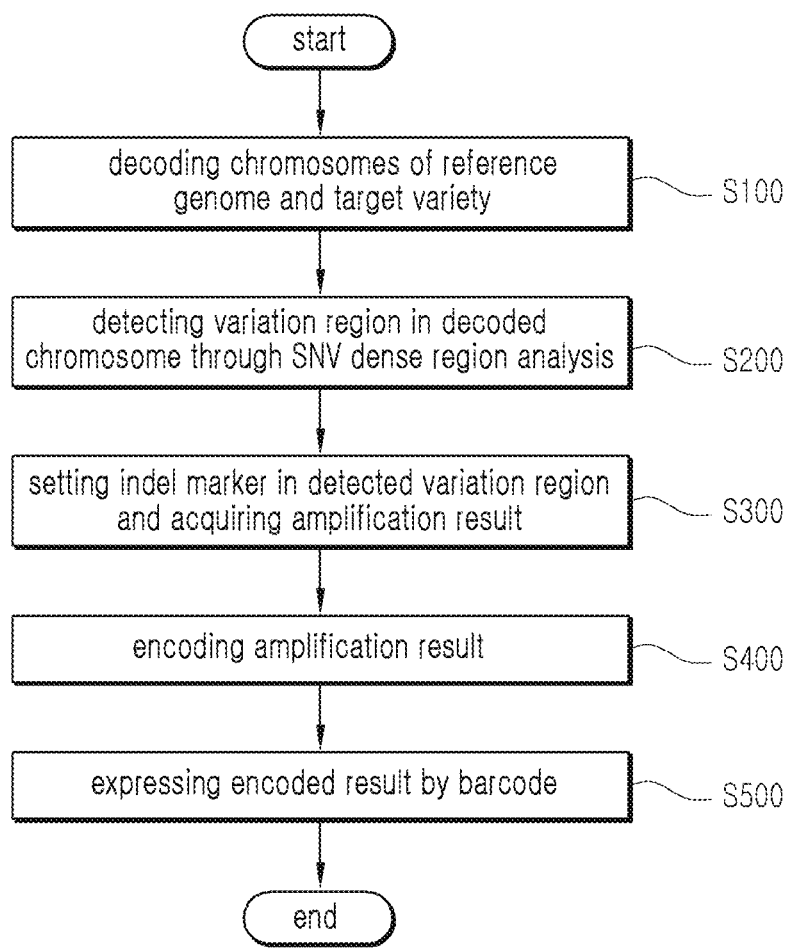
FIG. 2 is a flowchart of a variety identification-encoding method.
Figure 3:
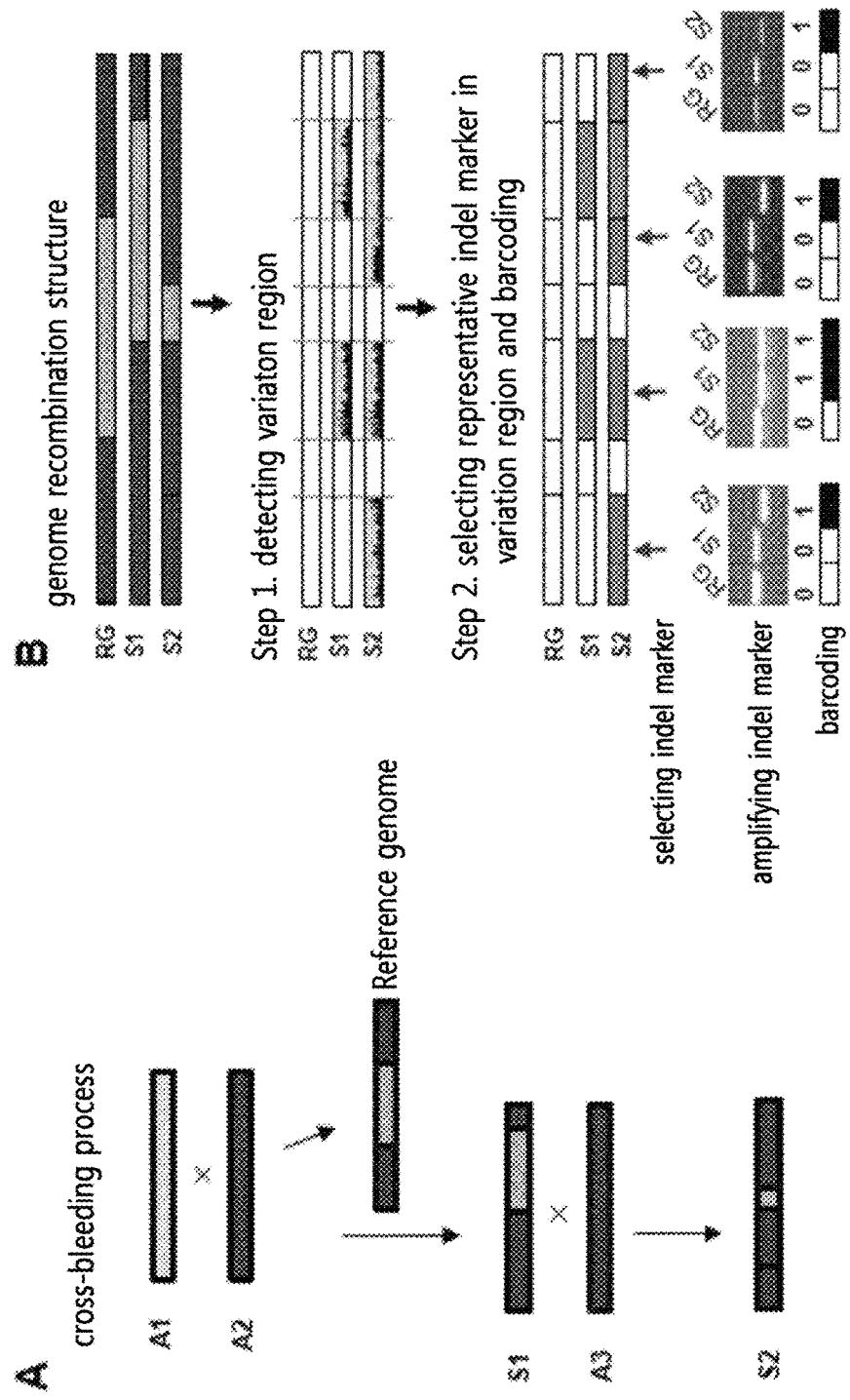
FIG. 3 is a view showing a stepwise development process of the variety identification-encoding system according to the present invention.

Next, a variety identification-encoding method according to the present invention will be described with reference to FIG. 2.

First, the chromosome-decoding module 100 decodes the chromosome of a reference genome variety and the chromosomes of target varieties (S100).

Next, the variation region-detecting module 200 detects variation regions from the decoded chromosome through single nucleotide variation (SNV) dense region analysis (S200). The specific method of detecting the variation regions has been described in the aforementioned system. Here, a reference genome variety is necessarily required. As the reference genome variety, preferably, in the case of beans, Williams 82 may be used, and, in the case of rice, Hwayeongbyeo may be used. However, the present invention is not limited thereto. Users can use desired varieties by directly setting reference varieties.

For example, when experiments are performed by using Daepung as a reference variety and using a new variety for developing a certification barcode as a comparative variety, first, the PCR is performed by indel markers developed for the two varieties, and then the amplification results are decoded. In this case, when the band sizes of the two varieties are the same as each other, it is represented by "a", and, when the band sizes thereof are different from each other, it is represented by "b". Then, the secured reference genome information is compared with Daepung, and data about the comparative variety is converted based on the reference genome, thereby encoding the target variety.

Here, when the band size of an amplification result of a reference genome variety is the same as the band size of an amplification result of a target variety, the amplification result is represented by "a", and when the band size of an amplification result of a reference genome variety is different from the band size of an amplification result of a target variety, the amplification result is represented by "b". Here, the amplification results are limited to "a" or "b" as long as they are different from each other according to the band size.

Next, the amplification result-acquiring module 300 sets indel markers in the detected variation regions and amplified the set indel markers by PCR to acquire amplification results (S300). The specific method of acquiring the amplification results has been described in the aforementioned system.

Next, the encoding module 400 encodes the amplification results thereof (S400).

Here, the encoding module 400 converts the amplification result "a" into a digital signal "0" to be marked with white, and converts the amplification result "b" into a digital signal "1" to be marked with black. Further, on the contrary, the encoding module 400 marks the digital signal "0" with white, and marks the digital signal "1" with black. However, the color thereof is not limited.

In this way, the output module 500 can express the encoded results as a barcode.

Further, users can selectively output the encoded results by a one-dimensional expression and a two-dimensional expression.

Further, users input the phenotype of a target variety through the phenotype input module 510 to output the phenotype of the target variety together with the encoded results (S500).

Meanwhile, the encoded results may be outputted only by the barcode. However, in an embodiment, two or more encoded results are outputted by a two-dimensional expression, but information about female or male varieties may also be outputted as a linage tree. In this way, a degree of recombination can be easily determined, and thus varieties can be more effectively identified.

In another embodiment, the output module 500 outputs two or more encoded results by a two-dimensional expression, but can automatically or manually detect the differences between the two or more two-dimensional expressions and mark these differences with colors other than white and black to distinguish backcrossed varieties and recurrent parent varieties. In this way, the limitation in the identification of varieties using conventional molecular markers can be overcome, and two varieties having very high genetic similarity can also be identified.

In still another embodiment, the output module 500 outputs two or more encoded results by a two-dimensional expression, but can automatically or manually detect hetero regions and mark these hetero regions with colors other than white and black to distinguish the degree of immobilization of varieties. In this way, the rapid immobilization of separating and breeding lines becomes possible, and thus the present invention can contribute to the uniformity and stability of varieties.

The invention claimed is:

1. A variety identification-encoding method, comprising the steps of:
    (a) extracting DNA of a reference genome variety and a target variety by pulverization, centrifugation, and precipitation of tissue of a reference genome variety and a target variety;
    (b) decoding a base sequence of extracted DNA of the reference genome variety and a base sequence of extracted DNA of the target variety;
    (c) detecting a plurality of variation regions through single nucleotide variation dense region analysis, wherein a variation region is detected when the base sequence of the target variety is compared with the base sequence of the reference genome variety in units of 10 kb and a single nucleotide variation is more than 4 per 10 kb;
    (d) setting a plurality of indel markers having nucleotide sequence specific to the detected plurality of variation regions and amplifying the DNA of the reference genome variety and the target variety by a polymerase chain reaction (PCR) using the set indel markers to acquire an amplification result;
    (e) encoding the amplification result; and
    (f) outputting an encoded result for each of the plurality of variation regions for each DNA of each target variety for two or more target varieties by a two-dimensional expression,
    wherein, in the step (d), the amplification result is represented by "a" when the band size of an amplification result of the reference genome variety is the same as the band size of an amplification result of the target variety, and is represented by "b" when the band size of the amplification result of the reference genome variety is different from the band size of the amplification result of the target variety,
    wherein the step (e) includes the step of:
    (e1) converting the amplification result "a" into a digital signal "0" to be marked with white, and converting the amplification result "b" into a digital signal "1" to be marked with black,
    wherein the two or more encoded results are represented by the two-dimensional expression and information about a female or male variety thereof is outputted as a lineage tree.

2. The method according to claim 1, wherein the step (f) includes the step of: outputting the phenotype of the target variety together with the encoded result.

3. The method according to claim 1, wherein the step (f) includes the steps of:
    detecting regions having the differences between the two or more two-dimensional expressions; and
    marking the detected regions with colors other than white and black to distinguish backcrossed varieties and recurrent parent varieties and output these varieties.

4. The method according to claim 1, wherein the step (f) includes the steps of:
    detecting hetero regions; and
    marking the hetero regions with colors other than white and black to distinguish a degree of immobilization of varieties and output these varieties.

5. A variety identification-encoding system, comprising:
    a pulverizer pulverizing tissue of a reference genome variety and a target variety;
    a centrifuge centrifuging the pulverized tissue;
    a tube in which DNA is precipitated from supernatant obtained by the centrifuge,
    a chromosome-decoder decoding a base sequence of precipitated DNA of the reference genome variety and a base sequence of precipitated DNA of the target variety;
    a variation region-detector detecting a plurality of variation regions through single nucleotide variation dense region analysis, wherein a variation region is detected when the base sequence of the target variety is compared with the base sequence of the reference genome variety in units of 10 kb and a single nucleotide variation is more than 4 per 10 kb,
    wherein the system is operable to set a plurality of indel markers having a nucleotide sequence specific to the detected plurality of variation regions and amplify the DNA of the reference genome variety and the target variety by a polymerase chain reaction (PCR) using the set indel markers to acquire an amplification result; and
    an encoder encoding the amplification result,
    wherein the system is operable to acquire the amplification result as "a" when the band size of an amplification result of the reference genome variety is the same as the band size of an amplification result of the target variety, and acquire the amplification result as "b" when the band size of an amplification result of the reference genome variety is different from the band size of an amplification result of the target variety,
    wherein the encoder converts the amplification result "a" into a digital signal "0" to be marked with white, and converts the amplification result "b" into a digital signal "1" to be marked with black,
    wherein the system is further operable to output an encoded result for each of the plurality of variation regions for each DNA of each target variety for two or more target varieties encoded by the encoder by a two-dimensional expression, and output information about a female or male variety thereof as a lineage tree.

6. The system according to claim 5, wherein the system is further operable to receive a phenotype of the target variety and output the phenotype thereof.

7. The system according to claim 5, wherein the system is further operable to output the two or more encoded results by a two-dimensional expression, and detect regions having the differences between the two or more two-dimensional expressions to mark the detected regions with colors other than white and black.

8. The system according to claim 5, wherein the system is operable to output the two or more encoded results by a two-dimensional expression, and detect hetero regions to mark the hetero regions with colors other than white and black.

* * * * *